United States Patent
Yang et al.

(10) Patent No.: US 10,336,992 B2
(45) Date of Patent: Jul. 2, 2019

(54) METHODS FOR PURIFICATION OF ARYLSULFATASE A

(75) Inventors: Ying Yang, Bedford, MA (US); Yong Wang, Wayland, MA (US)

(73) Assignee: Shire Human Genetic Therapies, Inc., Lexington, MA (US)

(*) Notice: Subject to any disclaimer, the term of this patent is extended or adjusted under 35 U.S.C. 154(b) by 0 days.

(21) Appl. No.: 14/128,468

(22) PCT Filed: Jul. 9, 2012

(86) PCT No.: PCT/US2012/045927
§ 371 (c)(1),
(2), (4) Date: Mar. 14, 2014

(87) PCT Pub. No.: WO2013/009686
PCT Pub. Date: Jan. 17, 2013

(65) Prior Publication Data
US 2014/0205585 A1    Jul. 24, 2014

Related U.S. Application Data

(60) Provisional application No. 61/506,023, filed on Jul. 8, 2011.

(51) Int. Cl.
*C12N 9/16* (2006.01)
(52) U.S. Cl.
CPC ........ *C12N 9/16* (2013.01); *C12Y 301/06008* (2013.01)
(58) Field of Classification Search
CPC ..................................................... C12N 9/16
See application file for complete search history.

(56) References Cited

U.S. PATENT DOCUMENTS

| | | | |
|---|---|---|---|
| 6,197,507 | B1 | 3/2001 | Berg et al. |
| 6,812,339 | B1 | 11/2004 | Venter et al. |
| 7,232,670 | B2 | 6/2007 | D'Azzo et al. |
| 8,536,315 | B2 | 9/2013 | Fogh et al. |
| 2003/0199073 | A1 | 10/2003 | Fogh et al. |
| 2004/0126370 | A1 | 7/2004 | d'Azzo et al. |
| 2008/0003211 | A1 | 1/2008 | Fogh et al. |
| 2009/0246187 | A1 | 10/2009 | Nilsson |

FOREIGN PATENT DOCUMENTS

| | | |
|---|---|---|
| EP | 0456229 A2 | 11/1991 |
| JP | 2002517516 A | 6/2002 |
| WO | WO-1999037325 A2 | 7/1999 |
| WO | WO-1999064462 A1 | 12/1999 |
| WO | WO-2000067789 A1 | 11/2000 |
| WO | WO-2001007065 A2 | 2/2001 |
| WO | WO-2002040686 A2 | 5/2002 |
| WO | WO-2002098455 A2 | 12/2002 |
| WO | WO-2002099092 A2 | 12/2002 |
| WO | WO-2003002731 A1 | 1/2003 |
| WO | WO-2003/029403 A2 | 4/2003 |
| WO | WO-2003057179 A2 | 7/2003 |
| WO | WO-2003066669 A2 | 8/2003 |
| WO | WO-2005073367 A1 | 8/2005 |
| WO | WO-2005094874 A1 | 10/2005 |
| WO | WO-2006/031560 A2 | 3/2006 |
| WO | WO-2007112757 A2 | 10/2007 |
| WO | WO 2014/110246 A1 | 7/2014 |

OTHER PUBLICATIONS

Cummings et al, Protein chromatography on hydroxyapatite columns. Methods Enzymol. 2009; 463:387-404.*
Asenjo et al, Protein purification using chromatography: selection of type, modelling and optimization of operating conditions. J Mol Recognit. Mar.-Apr. 2009;22(2):65-76.*
Aronson et al., "Lysosomal degradation of Asn-linked glycoprotein," The FASEB Journal, 3: 2615-2622 (1989).
Austin et al., "Abnormal sulphatase activities in two human diseases (metachromatic leucodystrophy and gargoylism)," Biochem. J., 93: 15c-17c (1964).
Baum et al., "The assay of arylsulfatases A and B in human urine," Clin. Chim. Acta, 4: 453-455 (1959).
Ben-Yoseph et al., "The Interrelations between High- and Low-Molecular-Weight Forms of Normal and Mutant (Krabbe-Disease) Galactocerebrosidase," J. Biochem., 189: 9-15 (1980).
Berg et al., "Purification and characterization of Recombinant Human Lysosomal a-mannosidase," Molecular Genetics and Metabolism, 73: 18-29 (2001).
Bond et al., "Structure of a human lysosomal sulfatase," Structure, 5(2): 277-289 (1997).
Bostick et al., "Separation and Analysis of Arylsulfatase Isoenzymes in Body Fluids of Man," Clinical Chemistry, American Association for Clinical Chemistry, 24(8): 1305-1316 (1978).
Branden et al., "Introduction to Protein Structure," Garland Publishing Inc., New York, p. 247 (1991).
Braulke et al., "Insulin-like Growth Factors I and II Stimulate Endocytosis but Do Not Affect Sorting of Lysosomal Enzymes in Human Fibroblasts," The Journal of Biological Chemistry, 265(12): 6650-6655 (1990).
Braulke et al., "Sulfated Oligosaccharides in Human Lysosomal Enzymes," Biochemical and Biophysical Research Communications, 143(1): 178-185 (1987).
Coenen et al., "Morphological alterations in the inner ear of the arylsulfatase A-deficient mouse," Acta Neuropathol, 101: 491-498 (2001).
Current Protocols in Protein Science, John Wiley & Sons, Inc., Unit 5.10 (1998).
D'Hooge et al., "Hyperactivity, neuromotor defects, and impaired learning and memory in a mouse model for metachromatic leukodystrophy," Brain Research, 907: 35-43 (2001).

(Continued)

*Primary Examiner* — Sheridan Swope
(74) *Attorney, Agent, or Firm* — Proskauer Rose LLP; Fangli Chen

(57) ABSTRACT

Methods of producing arylsulfatase A are described herein. The methods can include one or more steps of chromatography. Exemplary chromatographic steps include ion exchange chromatography, mixed mode chromatography, and hydrophobic interaction chromatography. Compositions containing and methods using arylsulfatase A produced by the methods described herein are also disclosed.

5 Claims, No Drawings

(56) References Cited

OTHER PUBLICATIONS

Demeule et al., "High transcytosis of melanotransferrin (P97) across the blood-brain barrier," Journal of Neurochemistry, 83: 924-933 (2002).
Dierks et al., "Conversion of cysteine to formylglycine: A protein modification in the endoplasmic reticulum," Proc. Natl. Acad. Sci. USA, 94: 11963-11968 (1997).
Dunican et al., "Designing Cell-Permeant Phosphopeptides to Modulate Intracellular Signaling Pathways," Biopolymers (Peptide Science), 60: 45-60 (2001).
Farooqui et al., "Isolation, Characterization and the Role of Rabbit Testicular Arylsulphatase A in Fertilization," Biochem. J., 181: 331-337 (1979).
Fluharty et al., "[58] Arylsulfatases A and B from Human liver," Meth. Enzymol., 50: 537-547 (1978).
Franco et al., "A Cluster of Sulfatase Genees on Xp22.3: Mutations in Chrondrodysplasia Punctata (CDPX) and Implications for Warfarin Embryopathy," Cell, 81: 15-25 (1995).
Gieselmann et al., "Arylsulfatase A pseudodeficiency: Loss of a polyadenylylation signal and N-glycosylation site," Proc. Natl. Acad. Sci. USA, 86(9436-9440 (1989).
Gieselmann et al., "In Vitro Mutagenesis of Potentioal N-Glycosylation Sites of Arylsulfatase A," Journal of Biological Chemistry, 267(19): 13262-13266 (1992).
Gieselmann et al., Metaachromatic leukodystrophy: consequences of sulphatide accumulation, Acta Paediatr Suppl., 443: 74-79 (2003).
Gieselmann et al., "Metachromatic leukodystrophy: Molecular genetics and an animal model," J. Inher. Metab. Dis., 21: 564-574 (1998).
Hallmann et al., "An inducible arylsulfatase of Volvox carteri with properties suitable for a reporter-gene system," Eur. J. Biochem., 221: 143-150 (1994).
Hess, et al., "Isolation and comparison of arylsulfatase A from rat liver and Morris hepatoma 7777," Eur. J. Biochem., 135: 505-509 (1983).
Hess et al., "Phenotype of arylsufatase A-deficient mice: Relationship to human metachromatic leukodystrophy," Proc. Natl. Acad. Sci. USA, 93: 14821-14826 (1996).
Hift et al., "Variegate porphyria in South Africa, 1688-1996—new developments in an old disease," S. Afr. Med. J., 87(6): 722-731 (1997).
Ho et al., "Synthetic Protein Transduction Domains: Enhanced Transduction Potential in Vitro and in Vivo," Cancer Research, 61: 474-477 (2001).
International Search Report for PCT/US2012/045927 (4 pages), dated Nov. 1, 2013.
James, Gordon T., "Essential Arginine Residues in Human Liver Arylsulfatase A," Archives of Biochemistry and Biophysics, 197(1): 57-62 (1979).
Jordon et al., "Purification, crystallization and properties of porphobilinogen deaminase from a recombiant strain of *Escherichia coli* K12," Biochem, 254: 427-435 (1988).
Kakkis et al., Abstract only, Abstract No. 281-0, "A Method to Reduce the Immune REsponse to Enzyme Replacement Therapy: Studies of Criteria for Success," J. Inherit. Metab. Dis., 26(2) (2003).
Kakkis et al., Abstract only, Abstract No. 282-0, "Effective Reduction of Lysosomal Storage in Brain and Meninges Following Intrathecal Administration of Iduronidase in Canine Mucopolysaccharidosis I (MPS I)," J. Inherit. Metab. Dis.
Kaneda et al., "Regional assignment of five genes of human chromosome 19," Chromosoma (BerJ), 95: 8-12 (1987).
Kelly et al., "Presence of a lysosomal enzyme, arylsulfatase-A, in the prelysosome-endosome compartments of human cultured fibroblasts," European Journal of Cell Biology, 48: 71-78 (1989).
Kudoh et al., "Diagnosis of Metachromatic Leukodystrophy, Krabbe Disease, and Farber Disease after Uptake of Fatty Acid-labeled Cerobroside Sulfate into Cultured Skin Fibroblasts," J. Clin. Invest., 70: 89-97 (1982).

Lee et al., "Evidence for an Essential Histidine Residue in Rabbit Liver Aryl Sulfatase A," Archives of Biochemistry and Biophysics, 171: 424-434 (1975).
Liao et al., "Cloning, Expression, Purification and Characterization of the Human Blood Specificity Lysosomal Acid a-Mannosidase," The Journal of Biological Chemistry, 271(45): 28348-28358 (1996).
Lindgren et al., "Cell-penetrating peptides," TIPS, 21: 99-103 (2000).
Lukatela et al., "Crystal Structure of Human Arylsufatase A: The Aldehyde Function and the Metal Ion at the Active Site Suggest a Novel Mechanism for Sulfate Ester Hydrolysis," Biochemistry, 37: 3654-3664 (1998).
Lüllmann-Rauch et al., "Lysosomal sulfoglycolipid storage in the kidneys of mice deficient for arylsulfatase A (ASA) and of double-knockout mice deficient for ASA and galactosylceramide synthase," Histochem Cell Biol., 116: 161-169 (2001).
Matsushima et al., "Absence of MHC Class II Molecules Reduces CNS Demyelination, Microglial/Macrophage Infiltration, and Twitching in Murine Globoid Cell Leukodystrophy," Cell, 78: 645-656 (1994).
Matzner et al., "Bone marrow stem cell-based gene transfer in a mouse model for metachromatic leukodystrophy: effects on visceral and nervous system disease manifestations," Gene Therapy, 9: 53-63 (2002).
Matzner et al., "Enzyme replacement improves nerve system pathology and function in a mouse model for metachromatic leukodystrophy," Human Molecular Genetics, 14: 1139-1152 (2005).
Matzner et al., "Long-term expression and transfer of arylsulfatase A into brain of arylsulfatase A-deficient mice transplanted with bone marrow expressing the arylsulfatase A cDNA from a retroviral vector," Gene Therapy, 7: 1250-1257 (2000).
Matzner et al., "Retrovirally expressed human arylsulfatase A corrects the metabolic defect of arylsulfatase A-deficient mouse cells," Gene Therapy, 7: 805-812 (2000).
Meissner et al., "Allosteric Inhibition of Human Lymphoblast and Purified Porphobilinogen Deaminase by Protoporphyrinogen and Coproporphyrinogen," J. Clin. Invest., 91: 1436-1444 (1993).
Meissner et al., "Protoporphyrinogen oxidase and porphobilinogen deaminase in variegate porphyria," European Journal of Clinical Investigation, 16: 257-261 (1986).
Millipore, "Protein Concentration and Diafiltration by Tangential Flow Filtration," Millipore Corporation, Billerica, MA 01821, USA (2003).
Muschol et al., "Secretion of phosphomannosyl-deficient arylsulphatase A and cathepsin D from isolated human macrophages," Biochem J., 368: 845-853 (2002).
Nebes et al., "Human Lysosomal Alpha-Mannosidase: Isolation and Nuceotide Sequence of the Full-Length cDNA," Biochemical and Biophysical Research Communications, 200(1): 239-245 (1994).
Nilssen et al., "a-Mannosidosis: functional cloning of the lysosomal a-mannosidase cDNA and identification of a mutation in two affected siblings," Human Molecular Genetics, 6(5): 717-726 (1997).
Pan et al., "TNF α Transport across the Blood-Brain Barrier is Abolished in Receptor Knockout Mice," Experimental Neurology, 174: 193-200 (2002).
Pan et al., "Upregulation of the Transport System for TNF α at the Blood-Brain Barrier," Archives of Physiology and Biochemistry, 109(4): 350-353 (2001).
Pearson et al., "Improved tools for biological sequence comparison," Procl Natl Acad Sci USA, 85: 2444-2448 (1988).
Pearson, William R., "(5) Rapid and Sensitive Sequence Comparison with FASTP and FASTA," Methods of Enzymology, 183: 63-98 (1990).
Perusi et al., "A novel mutation which represents the fifth non-pathogenic polymorphism in the coding sequence of the Arylsulfatase A gene," Molecular and Cellular Probes, 11: 449-451 (1997).
Peters et al., "Phylogenetic Conservation of Arylsulfatases," The Journal of Biological Chemistry, 265(6): 3374-3381 (1990).
Pohl, Thomas, "(7) Concentration of Proteins and Removal of Solutes," Methods in Enzymology, 182: 68-83 (1990).
Protein Purification Handbook, GE Healthcare (Oct. 2001).
Rafi et al., "Disease-causing mutations in cis with teh common arylsulfatase A pseudodeficiency allele compound the difficulties in

(56) References Cited

OTHER PUBLICATIONS accurately identifying patients and carriers of metachromatic leukodystrophy," Molecular Genetics and Metabolism, 79: 83-90 (2003).

Ricketts et al., "The R496H Mutation of Arylsulfatase A Does Not Cause Metachromatic Leukodystrophy," Human Mutation, 12: 238-239 (1998).

Riise et al., Genomic Structure of the Human Lysosomal a-Mannosidase Gene (MANB), Genomics, 42: 200-207 (1997).

Rodman et al., "Circulating natural IgM antibodies and their corresponding human cord blood cell-derived Mabs specifically combat the Tat protein of HIV," Experimental Hematology, 29: 1004-1009 (2001).

Rothenberger et al., "Coincident expression and distribution of melanotransferrin and transferring receptor in human brain capillary endothelium," Brain Research, 712: 117-121 (1996).

Sakai et al., "Purification and Characterization of Galactocerebrosidase from Human Lymphocytes," J. Biochem, 116(3): 615-620 (1994).

Sandhoff et al., "Kidney Sulfatides in Mouse Models of Inherited Glycosphingolipid Disorders," The Journal of Biological Chemistry, 277(23): 20386-20398 (2002).

Sangalli et al., "Transduced Fibroblasts and Metachromatic Leukodystrophy Lymphocytes Transfer Arylsulfatase A to Myelinating Glia and Deficient Cells in Vitro," Human Gene Therapy, 9: 2111-2119 (1998).

Sarafian et al., "Studies on the Charge Isomers of Arylsulfatase A," Biochemical Medicine, 33: 372-380 (1985).

Schmidt et al., "A Novel Amino Acid Modification in Sulfatases That is Defective in Multiple Sulfatase Deficiency," Cell, 82: 271-278 (1995).

Schröder et al., "Site-specific analysis of N-linked oligosaccharides of recombinant lysosomal arylsufatase A produced in different cell lines," Glycobiology, 20(2): 248-259 (2010).

Schuchman et al., "Human Arylsulfatase B: MOPAC Cloning, Nucleotide Sequence of a Full-Length cDNA, and Regions of Amino Acid Identity with Arylsulfatases A and C," Genomics, 6: 149-158 (1990).

Schwarze et al., "Protein transduction: unrestricted delivery into all cells?," trends in Cell Biology, 10: 290-295 (2000).

Scott et al., "Differential Staining of Acid Glycosaminoglycans (Mucopolysaccharides) by Alcian Blue in Salt Solutions," Histochemie, 5: 221-233 (1965).

Selmer et al., "The evolutionary conversation of a novel protein modification, the conversion of cysteine to serinesemialdehyde in arylsulfatase from Volvox carteri," Eur. J. Biochem., 238: 341-345 (1996).

Sevin et al., "Intracerebral adeno-associated virus-mediated gene transfer in rapidly progressive forms of metachromatic leukodystrophy," Human Molecular Genetics, 15(1): 53-64 (2006).

Shire et al., "Challenges in the Development of High Protein Concentration Formulations," Journal of Pharmaceutical Sciences, 93(6): 1390-1402 (2004).

Sofer et al., "Preparative chromatographic separation in pharmacuetical, diagnostic, and biotechnology industries: current and future trends," J. Chromatogr. A., 707(1): 23-28 (1995).

Sommerlade et al., "Four monoclonal antibodies inhibit the recognition of arylsulphatase A by the lysosomal enzyme phosphotransferase," Biochem J., 297: 123-130 (1994).

Stein et al., "Cloning and Expression of Human Arylsulfatase A," The Journal of Biological Chemistry, 264(2): 1252-1259 (1989).

Stevens et al., "Purification and Properties of Arylfulfatase A from Human Urine," The Journal of Biological Chemistry, 250(7): 2495-2501 (1975).

Thompson et al., "CIUSTAI W: improving the sensitivity of progressive multiple sequence alignment through sequence weighting, position-specific gap penalties and weight matrix choice," Nucleic Acids Research, 22(22): 4673-4680 (1994).

Tollersrud et al., "Purification of bovine lysosomal a-mannosidase, characterization of its gene and determination of two mutations that cause a-mannosidosis," Eur. J. Biochem, 246: 410-419 (1997).

Treuheit et al., "Inverse Relationship of Protein Concentration and Aggregation," Pharmaceutical Research, 19(4): 511-516 (2002).

Wada et al., "Microglial activation precedes acute neurodegeneration in Sandhoff disease and is suppressed by bone marrow transplantation," Proc. Natl. Acad Sci. (USA), 97(20): 10954-10959 (2000).

Waheed et al., "Phosphorylation and sulfation of arylsulfatase A accompanies biosynthesis of the enzyme in normal and carcinoma cell lines," Biochimica et Biophysica Acta, 847: 53-61 (1985).

Wang et al., "Erythropoietin production from CHO cells grown by continuous culture in a fluidized-bed bioreactor," Biotechnol. Bioeng., 77(2): 194-203 (2002).

Wittke et al., "Lysosomal sulfatide storage in the brain of arylsulfatase A-deficient mice: cellular alterations and topographic distribution," Acta Neurophatol, 108: 261-271 (2004).

Wu et al., "Neuroprotection with noninvasive neurotrophin delivery to the brain," Proc. Natl. Acad. Sci. USA, 96: 254-259 (1999).

Yao et al., "Microanalysis of Complex Tissue Lipids by High-Performance Thin-Layer Chromotography," Analytical Biochemistry, 150: 111-116 (1985).

Zielasek et al., "Functional Abnormalities in $P_0$-Deficient Mice Resemble Human Hereditary Neuropathies LInked to $P_0$ Gene Mutations," Muscle & Nerve, 19: 946-952 (1996).

Chen et al., "Galactocerebrosidase from human urine: purification and partial characterization," Biochimica et Biophysica Acta, 1170: 53-61 (1993).

Ida, et al., "Pathological and biochemical studies of fetal Krabbe disease," Brain & Development, 16: 480-484 (1994).

\* cited by examiner

METHODS FOR PURIFICATION OF ARYLSULFATASE A

CROSS-REFERENCE TO RELATED APPLICATIONS

This application is a 35 U.S.C. § 371 National Stage Application of International Application No. PCT/US2012/045927, filed Jul. 9, 2012, which claims priority to U.S. Provisional Patent Application Ser. No. 61/506,023, filed Jul. 8, 2011, the entire contents of which are incorporated by reference.

BACKGROUND

Metachromatic leukodystrophy (MLD) is caused by an autosomal recessive genetic defect in the lysosomal enzyme arylsulfatase A (ASA or ARSA), resulting in a progressive breakdown of membranes of the myelin sheath (demyelination) and accumulation of galactosyl sulphatide (cerebroside sulfate) in the white matter of both central nervous system (CNS) and peripheral nervous system. Patients with metachromatic leukodystrophy can be treated with enzyme replacement therapy (ERT) using recombinant arylsulfatase A (rASA).

SUMMARY

The disclosure relates, inter alia, to methods of producing arylsulfatase A. For example, the disclosure provides methods for purifying arylsulfatase A from a sample. The methods described herein can include one or more chromatographic steps. Exemplary chromatographic steps include, but not limited to, ion exchange chromatography (e.g., anion exchange and/or cation exchange chromatography), mixed mode chromatography, and hydrophobic chromatography. Further, compositions (e.g., pharmaceutical compositions) containing and methods using arylsulfatase A produced by the methods described herein are disclosed.

In one aspect, the disclosure features a method for purifying arylsulfatase A from a sample. The method includes, for example, providing a sample of arylsulfatase A (e.g., recombinant arylsulfatase A), and subjecting the sample to anion exchange chromatography, e.g., anion exchange chromatography described herein. In some embodiments, the anion exchange chromatography includes quaternary amine anion exchange chromatography. The anion exchange chromatography can be performed using, e.g., Q SEPHAROSE™ Fast Flow, Q SEPHAROSE™ High Performance, Q SEPHAROSE™ XL, CAPTO™ Q, DEAE, TOYOPEARL GIGACAP® Q, FRACTOGEL® TMAE, ESHMUNO™ Q, NUVIA™ Q, or UNOSPHERE™ Q.

In some embodiments, subjecting the sample of arylsulfatase A to anion exchange chromatography includes: loading the sample of arylsulfatase A onto an anion chromatography column, washing the anion exchange chromatography column, and eluting the arylsulfatase A from the column.

In some embodiments, loading the sample of arylsulfatase A onto the anion exchange chromatography column is performed with a loading buffer. In one embodiment, the loading buffer does not contain sodium chloride. In another embodiment, the loading buffer contains sodium chloride. For example, the sodium chloride concentration of the loading buffer is from about 1 mM to about 25 mM, e.g., from about 1 mM to about 10 mM, from about 1 mM to about 5 mM, or from about 5 mM to about 10 mM.

In some embodiments, loading the sample of arylsulfatase A onto the anion exchange chromatography column is performed at a pH from about 5 to about 9, e.g., from about 6 to about 8, e.g., about 7.

In some embodiments, the sample of arylsulfatase A is loaded onto the anion exchange chromatography column at a binding capacity about 15 g/L resin or less, e.g., about 10 g/L resin or less, about 5 g/L resin or less, or about 2 g/L resin or less, e.g., between about 2 g/L resin and about 5 g/L resin, between about 5 g/L resin and about 10 g/L resin, or between about 10 g/L resin and about 15 g/L resin.

In some embodiments, washing the anion exchange chromatography column is performed with one or more washing buffers. For example, washing the anion exchange column can include two or more (e.g., a first and a second) washing steps, each using a different washing buffer.

In one embodiment, the washing buffer does not contain sodium chloride. In another embodiment, the washing buffer contains sodium chloride. For example, the sodium chloride concentration of the washing buffer is from about 50 mM to about 200 mM, e.g., from about 50 mM to about 150 mM, from about 100 mM to about 200 mM, or from about 100 mM to about 150 mM, e.g., about 80 mM, about 100 mM, about 120 mM, or about 140 mM.

In some embodiments, washing the anion exchange chromatography column is performed at a pH from about 5 to about 9, e.g., from about 6 to about 8, e.g., about 7.

In some embodiments, eluting the arylsulfatase A from the anion exchange chromatography column is performed with an elution buffer.

In some embodiments, the elution buffer contains sodium chloride. For example, the sodium chloride concentration of the elution buffer is from about 100 mM to about 500 mM, e.g., from about 100 mM to about 300 mM, or about 200 mM to about 400 mM, e.g., about 180 mM, about 200 mM, about 220 mM, about 240 mM, about 260 mM, or about 280 mM.

In some embodiments, eluting the arylsulfatase A from the anion exchange chromatography column is performed at a pH from about 5 to about 9, e.g., from about 6 to about 8, e.g., about 7.

In some embodiments, eluting the arylsulfatase A from the anion exchange chromatography column includes one or more steps of elution peak collection. For example, the elution peak collection starts from about 50 mAU at the ascending side to about 50 mAU at the descending side, e.g., from about 100 mAU at the ascending side to about 50 mAU at the descending side, from about 200 mAU at the ascending side to about 50 mAU at the descending side, from about 50 mAU at the ascending side to about 100 mAU at the descending side, from about 50 mAU at the ascending side to about 200 mAU at the descending side, or from about 100 mAU at the ascending side to about 100 mAU at the descending side, e.g., as determined by spectrophotometry, e.g., at 280 nM.

The loading buffer, washing buffer, and elution buffer described herein can include one or more buffering agents. For example, the buffering agent can be TRIS, HEPES, MOPS, PIPES, SSC, MES, sodium phosphate, sodium acetate, or a combination thereof. The concentration of the buffering agent is between about 1 mM and about 500 mM, e.g., between about 10 mM and about 250 mM, between about 20 mM and about 100 mM, between about 1 mM and 5 mM, between about 5 mM and 10 mM, between about 10 mM and 50 mM, or between about 50 mM and about 100 mM, e.g., about 1 mM, about 5 mM, about 10 mM, about 20 mM, about 30 mM, about 40 mM, or about 50 mM.

In some embodiments, subjecting the sample of arylsulfatase A to the anion exchange chromatography is performed at a temperature about 23° C. or less, about 18° C. or less, or about 16° C. or less, e.g., about 23° C., about 20° C., about 18° C., or about 16° C.

In one embodiment, the arylsulfatase A is purified on a bench scale. In another embodiment, the arylsulfatase A is purified on a manufacturing scale.

In some embodiments, the arylsulfatase A activity yield is at least about 75%, e.g., at least about 85%, e.g., between about 85% and about 99% or between about 90% and about 99%.

In some embodiments, the protein yield (AU or Absorbance Units) is from about 10% to 50%, e.g., from about 20% to about 35%, or from about 25% to about 30%, e.g., as determined by spectrophotometry, e.g., at 280 nm.

In some embodiments, the host cell protein (HCP) log reduction value (LRV) is between about 0.5 and about 1.0, e.g., between about 0.6 and 0.9, or between about 0.7 and 0.8.

In some embodiments, the method further includes subjecting the sample of arylsulfatase A to mixed mode chromatography, which may include, for example, ceramic hydroxyapatite (HA) chromatography, e.g., hydroxyapatite type I or type II chromatography, e.g., as described herein. In some embodiments, the sample of arylsulfatase A is subjected to anion exchange chromatography prior to the mixed mode chromatography.

In some embodiments, the method further includes subjecting the sample of arylsulfatase A to hydrophobic interaction chromatography (HIC), e.g., phenyl chromatography, e.g., as described herein. In some embodiments, the sample of arylsulfatase A is subjected to anion exchange chromatography prior to HIC.

In some embodiments, the method further includes subjecting the sample of arylsulfatase A to cation exchange chromatography, e.g., sulfopropyl (SP) cation exchange chromatography, e.g., as described herein. In some embodiments, the sample of arylsulfatase A is subjected to anion exchange chromatography prior to cation exchange chromatography.

In some embodiments, a method further includes capturing the sample of arylsulfatase A, e.g., by a method that includes tangential flow ultrafiltration.

In some embodiments, the method further includes subjecting the sample of arylsulfatase A to depth filtration, e.g., using a ZETA PLUS® depth filter.

In some embodiments, the method further includes subjecting the sample of arylsulfatase A to viral inactivation. In one embodiment, the viral inactivation comprises a solvent and/or a detergent. The solvent or detergent can include, for example, polysorbate 80, Tri-n-Butyl-Phosphate (TnBP), or both. In another embodiment, the viral inactivation comprises virus filtration, e.g., by using a PLANOVA™ filter.

In some embodiments, the method further comprises concentrating and/or filtering the sample of arylsulfatase A, e.g., by ultrafiltration and/or diafiltration, e.g., by tangential flow ultrafiltration.

In some embodiments, the specific activity of the purified arylsulfatase A is at least from about 50 U/mg to about 140 U/mg, e.g., at least about 70 U/mg, at least about 90 U/mg, at least about 100 U/mg, or at least about 120 U/mg, e.g., as determined by a method described herein.

In some embodiments, the arylsulfatase A is purified to at least about 95%, at least about 98%, at least about 99%, at least about 99.5%, at least about 99.6%, at least about 99.7%, at least about 99.8%, or at least about 99.9%. The purity of arylsulfatase A can be measured by, e.g., one or more of: host cell protein (HCP) Western blot, SDS-PAGE Coomassie staining, SDS-PAGE silver staining, reverse phase HPLC, and size exclusion HPLC.

In some embodiments, the method further includes formulating the purified arylsulfatase A. The buffer used for formulating the purified arylsulfatase A can include, for example, sodium chloride.

In one aspect, the disclosure features a method of purifying arylsulfatase A from a sample, where the method includes, for example, providing a sample of arylsulfatase A (e.g., recombinant arylsulfatase A), and subjecting the sample of arylsulfatase A to mixed mode chromatography, e.g., mixed mode chromatography described herein, such as a method including ceramic hydroxyapatite (HA) chromatography, e.g., hydroxyapatite type I or type II chromatography. In some embodiments, the mixed mode chromatography is performed using one or more of: CHT™ Ceramic Hydroxyapatite Type I Media, CHT™ Ceramic Hydroxyapatite Type II Media, BIO-GEL® HT Hydroxyapatite, and BIO-GEL® HTP Hydroxyapatite.

In some embodiments, subjecting the sample of arylsulfatase A to mixed mode chromatography includes: loading the sample of arylsulfatase A onto a mixed mode chromatography column (e.g., HA chromatography), washing the mixed mode chromatography column, and eluting the arylsulfatase A from the column.

In some embodiments, loading the sample of arylsulfatase A onto the mixed mode chromatography column is performed with a loading buffer. In one embodiment, the loading buffer contains sodium phosphate. For example, the sodium phosphate concentration of the loading buffer is from about 1 mM to about 10 mM, e.g., from about 1 mM to about 5 mM, from about 5 mM to about 10 mM, e.g., about 1 mM, about 2 mM, or about 5 mM. In another embodiment, the loading buffer contains sodium chloride. For example, the sodium chloride concentration of the loading buffer is from about 100 mM to about 400 mM, e.g., from about 200 to about 300 mM, e.g., about 220 mM, about 240 mM, about 260 mM, or about 280 mM.

In some embodiments, loading the sample of arylsulfatase A onto the mixed mode chromatography column is performed at a pH from about 5 to about 9, e.g., from about 6 to about 8, e.g., about 7.

In some embodiments, the sample of arylsulfatase A is loaded onto the anion exchange chromatography column at a binding capacity about 23 AU/L resin or less, e.g., about 19 AU/L resin or less, about 15 AU/L resin or less, or about 12 AU/L resin or less, e.g., between about 12 AU/L resin and about 15 AU/L resin, or between about 15 AU/L resin and about 19 AU/L resin.

In some embodiments, washing the mixed mode chromatography column is performed with one or more washing buffers. For example, washing the mixed mode chromatography column can include two or more (e.g., a first and a second) washing steps, each using a different washing buffer.

In one embodiment, the washing buffer contains sodium phosphate. For example, the sodium phosphate concentration of the washing buffer is from about 1 mM to about 10 mM, e.g., from about 1 mM to about 5 mM, from about 5 mM to about 10 mM, e.g., about 1 mM, about 5 mM, or about 10 mM. In another embodiment, the washing buffer contains sodium chloride. For example, the sodium chloride concentration of the washing buffer is from about 50 mM to about 600 mM, e.g., from about 100 mM to about 500 mM, or from about 200 to about 400 mM, e.g., about 220 mM, about 240 mM, about 260 mM, or about 280 mM.

In some embodiments, washing the mixed mode chromatography column is performed at a pH from about 5 to about 9, e.g., from about 6 to about 8, e.g., about 7.

In some embodiments, eluting the arylsulfatase A from the anion exchange chromatography column is performed with an elution buffer.

In one embodiment, the elution buffer contains sodium phosphate. For example, the sodium phosphate concentration of the elution buffer is from about 20 mM to about 50 mM, e.g., from about 25 mM to about 45 mM, e.g., about 30 mM, about 35 mM, or about 40 mM. In another embodiment, the elution buffer does not contain sodium chloride. In yet another embodiment, the elution buffer contains sodium chloride. For example, the sodium chloride concentration of the elution buffer is from about 200 mM to about 300 mM, e.g., from about 240 mM to about 280 mM.

In some embodiments, eluting the arylsulfatase A from the mixed mode chromatography column is performed at a pH from about 5 to about 9, e.g., from about 6 to about 8, e.g., about 7.

In some embodiments, eluting the arylsulfatase A from the mixed mode chromatography column includes one or more steps of elution peak collection. For example, the elution peak collection starts from about 50 mAU at the ascending side to about 50 mAU at the descending side, e.g., from about 100 mAU at the ascending side to about 50 mAU at the descending side, from about 200 mAU at the ascending side to about 50 mAU at the descending side, from about 50 mAU at the ascending side to about 100 mAU at the descending side, from about 50 mAU at the ascending side to about 200 mAU at the descending side, or from about 100 mAU at the ascending side to about 100 mAU at the descending side, e.g., as determined by spectrophotometry, e.g., at 280 nM.

The loading buffer, washing buffer, and elution buffer described herein can include one or more buffering agents. For example, the buffering agent can be TRIS, HEPES, MOPS, PIPES, SSC, MES, sodium phosphate, sodium acetate, or a combination thereof. The concentration of the buffering agent is between about 1 mM and about 500 mM, e.g., between about 10 mM and about 250 mM, between about 20 mM and about 100 mM, between about 1 mM and 5 mM, between about 5 mM and 10 mM, between about 10 mM and 50 mM, or between about 50 mM and about 100 mM, e.g., about 1 mM, about 5 mM, about 10 mM, about 20 mM, about 30 mM, about 40 mM, or about 50 mM.

In some embodiments, subjecting the sample of arylsulfatase A to the mixed mode exchange chromatography is performed at a temperature about 23° C. or less, about 18° C. or less, or about 16° C. or less, e.g., about 23° C., about 20° C., about 18° C., or about 16° C.

In one embodiment, the arylsulfatase A is purified on a bench scale. In another embodiment, the arylsulfatase A is purified on a manufacturing scale.

In some embodiments, the arylsulfatase A activity yield is at least about 80%, e.g., at least about 90%, e.g., between about 80% and about 115%.

In some embodiments, the protein yield (AU or Absorbance Units) is from about 30% to about 80%, e.g., from about 35% to about 75%, or from about 50% to about 70%, e.g., as determined by spectrophotometry, e.g., at 280 nm.

In some embodiments, the host cell protein (HCP) log reduction value (LRV) is between about 0.3 and about 0.6, e.g., between about 0.4 and 0.5.

In some embodiments, the method further includes subjecting the sample of arylsulfatase A to hydrophobic interaction chromatography (HIC), e.g., phenyl chromatography, e.g., as described herein. In some embodiments, the sample of arylsulfatase A is subjected to mixed mode chromatography prior to HIC.

In some embodiments, the method further includes subjecting the sample of arylsulfatase A to cation exchange chromatography, e.g., sulfopropyl (SP) cation exchange chromatography, e.g., as described herein. In some embodiments, the sample of arylsulfatase A is subjected to anion exchange chromatography prior to cation exchange chromatography.

In some embodiments, a method further includes capturing the sample of arylsulfatase A, e.g., by a method that includes tangential flow ultrafiltration.

In some embodiments, the method further includes subjecting the sample of arylsulfatase A to depth filtration, e.g., using a ZETA PLUS® depth filter.

In some embodiments, the method further includes subjecting the sample of arylsulfatase A to viral inactivation. In one embodiment, the viral inactivation comprises a solvent and/or a detergent. The solvent or detergent can include, for example, polysorbate 80, Tri-n-Butyl-Phosphate (TnBP), or both. In another embodiment, the viral inactivation comprises virus filtration, e.g., by using a PLANOVA™ filter.

In some embodiments, the method further comprises concentrating and/or filtering the sample of arylsulfatase A, e.g., by ultrafiltration and/or diafiltration, e.g., by tangential flow ultrafiltration.

In some embodiments, the specific activity of the purified arylsulfatase A is at least from about 50 U/mg to about 140 U/mg, e.g., at least about 70 U/mg, at least about 90 U/mg, at least about 100 U/mg, or at least about 120 U/mg, e.g., as determined by a method described herein.

In some embodiment, the arylsulfatase A is purified to at least about 95%, at least about 98%, at least about 99%, at least about 99.5%, at least about 99.6%, at least about 99.7%, at least about 99.8%, or at least about 99.9%. The purity of arylsulfatase A can be measured by, e.g., one or more of: host cell protein (HCP) Western blot, SDS-PAGE Coomassie staining, SDS-PAGE silver staining, reverse phase HPLC, and size exclusion HPLC.

In some embodiments, the method further includes formulating the purified arylsulfatase A. The buffer used for formulating the purified arylsulfatase A can include, for example, sodium chloride.

In another aspect, the disclosure provides a method of purifying arylsulfatase A from a sample, where the method includes, for example, providing a sample of arylsulfatase A (e.g., recombinant arylsulfatase A), and subjecting the sample of arylsulfatase A to hydrophobic interaction chromatography (HIC), e.g., hydrophobic interaction chromatography described herein. In one embodiment, the hydrophobic interaction chromatography includes phenyl chromatography. In other embodiments, the hydrophobic interaction chromatography includes butyl chromatography or octyl chromatography.

In some embodiments, the hydrophobic interaction chromatography includes phenyl chromatography using one or more of Phenyl SEPHAROSE™ High Performance, Phenyl SEPHAROSE™ 6 Fast Flow (low sub), or Phenyl SEPHAROSE™ 6 Fast Flow (high sub).

In some embodiments, subjecting the sample of arylsulfatase A to hydrophobic interaction chromatography includes: loading the sample of arylsulfatase A onto a HIC column, washing the HIC column, and eluting the arylsulfatase A from the column.

In some embodiments, loading the sample of arylsulfatase A onto the HIC column is performed with a loading buffer. In one embodiment, the loading buffer contains sodium chloride. For example, the sodium chloride concentration of the loading buffer is from about 0.5 M to about 2.5 M, e.g., about 1 M or about 1.5 M. In another embodiment, the loading buffer contains sodium phosphate. For example, the sodium phosphate concentration of the loading buffer is from about 10 mM to about 100 mM, e.g., about 25 mM, about 50 mM, or about 75 mM.

In some embodiments, loading the sample of arylsulfatase A onto the HIC column is performed at a pH from about 5 to about 7, e.g., from about 5.5 to about 6.5, e.g., about 5.5, about 6.0, or about 6.5.

In some embodiments, the sample of arylsulfatase A is loaded onto the HIC column at a binding capacity about 12 AU/L resin or less, e.g., about 10 AU/L resin or less, about 9 AU/L resin or less, about 7 AU/L resin or less, or about 5 AU/L resin or less, e.g., between about 5 AU/L resin and about 9 AU/L resin, or between about 5 AU/L resin and about 7 AU/L resin.

In some embodiments, washing the HIC column is performed with one or more washing buffers. For example, washing the HIC column can include two or more (e.g., a first and a second) washing steps, each using a different washing buffer.

In one embodiment, the washing buffer contains sodium chloride. For example, the sodium chloride concentration of the washing buffer is from about 100 mM to about 1.5 M, e.g., from about 250 mM to about 1 M, e.g., about 250 mM, about 500 mM, about 750 mM, or about 1M. In another embodiment, the washing buffer contains sodium phosphate. For example, the sodium phosphate concentration of the loading buffer is from about 10 mM to about 100 mM, e.g., about 25 mM, about 50 mM, or about 75 mM.

In some embodiments, washing the HIC column is performed at a pH from about 5 to about 7, e.g., from about 5.5 to about 6.5, e.g., about 5.5, about 6.0, or about 6.5.

In some embodiments, eluting the arylsulfatase A from the HIC column is performed with an elution buffer.

In some embodiments, the elution buffer contains sodium chloride. For example, the sodium chloride concentration of the elution buffer is from about 30 mM to about 100 mM, e.g., from about 45 mM to about 85 mM, e.g., about 50 mM, about 60 mM, about 70 mM, or about 80 mM.

In some embodiments, eluting the arylsulfatase A from the HIC column is performed at a pH from about 5 to about 9, e.g., from about 6 to about 8, e.g., about 7.

In some embodiments, eluting the arylsulfatase A from the HIC column includes one or more steps of elution peak collection. For example, the elution peak collection starts from about 50 mAU at the ascending side to about 50 mAU at the descending side, e.g., from about 100 mAU at the ascending side to about 50 mAU at the descending side, from about 200 mAU at the ascending side to about 50 mAU at the descending side, from about 50 mAU at the ascending side to about 100 mAU at the descending side, from about 50 mAU at the ascending side to about 200 mAU at the descending side, or from about 100 mAU at the ascending side to about 100 mAU at the descending side, e.g., as determined by spectrophotometry, e.g., at 280 nM.

The loading buffer, washing buffer, and elution buffer described herein can include one or more buffering agents. For example, the buffering agent can be TRIS, HEPES, MOPS, PIPES, SSC, MES, sodium phosphate, sodium acetate, or a combination thereof. The concentration of the buffering agent is between about 1 mM and about 500 mM, e.g., between about 10 mM and about 250 mM, between about 20 mM and about 100 mM, between about 1 mM and 5 mM, between about 5 mM and 10 mM, between about 10 mM and 50 mM, or between about 50 mM and about 100 mM, e.g., about 1 mM, about 5 mM, about 10 mM, about 20 mM, about 30 mM, about 40 mM, or about 50 mM.

In some embodiments, subjecting the sample of arylsulfatase A to HIC is performed at a temperature about 23° C. or less, about 18° C. or less, or about 16° C. or less, e.g., about 23° C., about 20° C., about 18° C., or about 16° C.

In one embodiment, the arylsulfatase A is purified on a bench scale. In another embodiment, the arylsulfatase A is purified on a manufacturing scale.

In some embodiments, the arylsulfatase A activity yield is at least about 60%, e.g., at least about 70%, e.g., between about 70% and about 100%.

In some embodiments, the protein yield (AU or Absorbance Units) is from about 45% to 100%, e.g., from about 50% to about 95%, or from about 55% to about 90%, e.g., as determined by spectrophotometry, e.g., at 280 nm.

In some embodiments, the host cell protein (HCP) log reduction value (LRV) is between about 0.6 and about 1.2, e.g., between about 0.7 and 0.95.

In some embodiments, the method further includes subjecting the sample of arylsulfatase A to cation exchange chromatography, e.g., sulfopropyl (SP) cation exchange chromatography, e.g., as described herein. In some embodiments, the sample of arylsulfatase A is subjected to HIC prior to cation exchange chromatography.

In some embodiments, a method further includes capturing the sample of arylsulfatase A, e.g., by a method that includes tangential flow ultrafiltration.

In some embodiments, the method further includes subjecting the sample of arylsulfatase A to depth filtration, e.g., using a ZETA PLUS® depth filter.

In some embodiments, the method further includes subjecting the sample of arylsulfatase A to viral inactivation. In one embodiment, the viral inactivation comprises a solvent and/or a detergent. The solvent or detergent can include, for example, polysorbate 80, Tri-n-Butyl-Phosphate (TnBP), or both. In another embodiment, the viral inactivation comprises virus filtration, e.g., by using a PLANOVA™ filter.

In some embodiments, the method further comprises concentrating and/or filtering the sample of arylsulfatase A, e.g., by ultrafiltration and/or diafiltration, e.g., by tangential flow ultrafiltration.

In some embodiments, the specific activity of the purified arylsulfatase A is at least from about 50 U/mg to about 140 U/mg, e.g., at least about 70 U/mg, at least about 90 U/mg, at least about 100 U/mg, or at least about 120 U/mg, e.g., as determined by a method described herein.

In some embodiment, the arylsulfatase A is purified to at least about 95%, at least about 98%, at least about 99%, at least about 99.5%, at least about 99.6%, at least about 99.7%, at least about 99.8%, or at least about 99.9%. The purity of arylsulfatase A can be measured by, e.g., one or more of: host cell protein (HCP) Western blot, SDS-PAGE Coomassie staining, SDS-PAGE silver staining, reverse phase HPLC, and size exclusion HPLC.

In some embodiments, the method further includes formulating the purified arylsulfatase A. The buffer used for formulating the purified arylsulfatase A can include, for example, sodium chloride.

In another aspect, the disclosure features a method of purifying arylsulfatase A from a sample, where the method includes, for example, providing a sample of arylsulfatase A (e.g., recombinant arylsulfatase A), and subjecting the sample to cation exchange chromatography, e.g., cation exchange chromatography described herein.

In one embodiment, the cation exchange chromatography includes sulfopropyl (SP) cation exchange chromatography. In another embodiment, the cation exchange chromatography is a polishing step. The cation exchange chromatography (e.g., sulfopropyl (SP) cation exchange chromatography) can be performed using, e.g., one or more of: TOYOPEARL® SP-650, TOYOPEARL® SP-550, TSK-GEL® SP-3PW, TSKGEL® SP-5PW, SP SEPHAROSE™ Fast Flow, SP SEPHAROSE™ High Performance, SP SEPHAROSE™ XL, SARTOBIND® S membrane, POROS® HS50, UNOSPHERE™ S, and MACROCAP™ S.

In some embodiments, subjecting the sample of arylsulfatase A to a cation exchange chromatography includes: loading the sample of arylsulfatase A onto a cation chromatography column (e.g., a sulfopropyl (SP) cation exchange column), washing the cation exchange chromatography column, and eluting the arylsulfatase A from the column.

In some embodiments, loading the sample of arylsulfatase A onto the cation exchange chromatography column is performed with a loading buffer. In one embodiment, the loading buffer contains sodium chloride. For example, the sodium chloride concentration of the loading buffer is from about 1 mM to about 25 mM, e.g., from about 5 mM to about 20 mM, e.g., about 5 mM, about 10 mM, about 15 mM, or about 20 mM. In another embodiment, the washing buffer contains sodium acetate. For example, the sodium acetate concentration of the loading buffer is from about 10 mM to about 100 mM, e.g., about 20 mM, about 40 mM, or about 60 mM.

In some embodiments, loading the sample of arylsulfatase A onto the cation exchange chromatography column is performed at a pH from about 3.0 and about 6.0, e.g., from about 4.0 and about 5.0, e.g., about 4.0, about 4.3, or about 4.5.

In some embodiments, the sample of arylsulfatase A is loaded onto the cation exchange chromatography column at a binding capacity about 15 AU/L resin or less, e.g., about 14 AU/L resin or less, or about 12 AU/L resin or less, e.g., between about 10 AU/L resin and about 14 AU/L resin, or between about 10 AU/L resin and about 12 AU/L resin.

In some embodiments, washing the cation exchange chromatography column is performed with one or more washing buffers. For example, washing the cation exchange column can include two or more (e.g., a first and a second) washing steps, each using a different washing buffer.

In one embodiment, the washing buffer contains sodium chloride. For example, the sodium chloride concentration of the loading buffer is from about 1 mM to about 25 mM, e.g., from about 5 mM to about 20 mM, or from about 10 mM to about 15 mM, e.g., about 5 mM, about 10 mM, about 15 mM, or about 20 mM. In another embodiment, the washing buffer contains sodium acetate. For example, the sodium acetate concentration of the loading buffer is from about 10 mM to about 100 mM, e.g., about 20 mM, about 40 mM, or about 60 mM.

In some embodiments, washing the cation exchange chromatography column is performed at a pH from about 3.0 and about 6.0, e.g., from about 4.0 and about 5.0, e.g., about 4.0, about 4.3, or about 4.5.

In some embodiments, eluting the arylsulfatase A from the cation exchange chromatography column is performed with an elution buffer.

In one embodiment, the elution buffer contains sodium chloride. For example, the sodium chloride concentration of the elution buffer is from about 25 mM to about 75 mM, e.g., from about 45 mM to about 60 mM, e.g., about 45 mM, about 50 mM, about 55 mM, or about 55 mM. In another embodiment, the washing buffer contains sodium acetate. For example, the sodium acetate concentration of the loading buffer is from about 10 mM to about 100 mM, e.g., about 20 mM, about 40 mM, or about 60 mM.

In some embodiments, eluting the arylsulfatase A from the cation exchange chromatography column is performed at a pH from about 3.0 and about 6.0, e.g., from about 4.0 and about 5.0, e.g., about 4.0, about 4.3, or about 4.5.

In some embodiments, eluting the arylsulfatase A from the cation exchange chromatography column includes one or more steps of elution peak collection. For example, the elution peak collection starts from about 50 mAU at the ascending side to about 50 mAU at the descending side, e.g., from about 100 mAU at the ascending side to about 50 mAU at the descending side, from about 200 mAU at the ascending side to about 50 mAU at the descending side, from about 50 mAU at the ascending side to about 100 mAU at the descending side, from about 50 mAU at the ascending side to about 200 mAU at the descending side, or from about 100 mAU at the ascending side to about 100 mAU at the descending side, e.g., as determined by spectrophotometry, e.g., at 280 nM.

The loading buffer, washing buffer, and elution buffer described herein can include one or more buffering agents. For example, the buffering agent can be TRIS, HEPES, MOPS, PIPES, SSC, MES, sodium phosphate, sodium acetate, or a combination thereof. The concentration of the buffering agent is between about 1 mM and about 500 mM, e.g., between about 10 mM and about 250 mM, between about 20 mM and about 100 mM, between about 1 mM and 5 mM, between about 5 mM and 10 mM, between about 10 mM and 50 mM, or between about 50 mM and about 100 mM, e.g., about 1 mM, about 5 mM, about 10 mM, about 20 mM, about 30 mM, about 40 mM, or about 50 mM.

In some embodiments, subjecting the sample of arylsulfatase A to the cation exchange chromatography is performed at a temperature about 23° C. or less, about 18° C. or less, or about 16° C. or less, e.g., about 23° C., about 20° C., about 18° C., or about 16° C. In some embodiments, subjecting the sample of arylsulfatase A to the cation exchange chromatography is performed between about 23° C. and about 16° C., e.g., at about 23° C., about 20° C., about 18° C., or about 16° C., and loading the sample of arylsulfatase A onto the cation exchange chromatography column is performed at a pH between about 4.5 and about 4.3, e.g., at about 4.5, about 4.4, or about 4.3. In some embodiments, subjecting the sample of arylsulfatase A to the cation exchange chromatography is performed at about 23° C. and loading the sample of arylsulfatase A onto the cation exchange chromatography column is performed at a pH about 4.5. In some embodiments, subjecting the sample of arylsulfatase A to the cation exchange chromatography is performed at about 23° C. and loading the sample of arylsulfatase A onto the cation exchange chromatography column is performed at a pH about 4.3. In some embodiments, subjecting the sample of arylsulfatase A to the cation exchange chromatography is performed at about 18° C. and loading the sample of arylsulfatase A onto the cation exchange chromatography column is performed at a pH about 4.5. In some embodiments, subjecting the sample of arylsulfatase A to the cation exchange chromatography is performed at about 18° C. and loading the sample of arylsulfatase A onto the cation exchange chromatography column is performed at a pH about 4.3.

In one embodiment, the arylsulfatase A is purified on a bench scale. In another embodiment, the arylsulfatase A is purified on a manufacturing scale.

In some embodiments, the arylsulfatase A activity yield is at least about 75%, e.g., at least about 80%, e.g., between about 80% and about 105%.

In some embodiments, the protein yield (AU or Absorbance Units) is from about 65% to 100%, e.g., from about 70% to about 95%, e.g., as determined by spectrophotometry, e.g., at 280 nm.

In some embodiments, the host cell protein (HCP) log reduction value (LRV) is between about 1.0 and about 2.5, e.g., between about 1.5 and about 2.0 or between about 1.7 and about 1.9.

The specific activity of the purified arylsulfatase A can be at least from about 50 U/mg to about 140 U/mg, e.g., at least about 70 U/mg, at least about 90 U/mg, at least about 100 U/mg, or at least about 120 U/mg, e.g., as determined by a method described herein.

In some embodiments, the arylsulfatase A is purified to at least about 95%, at least about 98%, at least about 99%, at least about 99.5%, at least about 99.6%, at least about 99.7%, at least about 99.8%, or at least about 99.9%. The purity of arylsulfatase A can be measured by, e.g., one or more of: host cell protein (HCP) Western blot, SDS-PAGE Coomassie staining, SDS-PAGE silver staining, reverse phase HPLC, and size exclusion HPLC.

In some embodiments, the method further includes capturing the sample of arylsulfatase A, e.g., by a method that includes tangential flow ultrafiltration.

In some embodiments, the method further includes subjecting the sample of arylsulfatase A to depth filtration, e.g., using a ZETA PLUS® depth filter.

In some embodiments, the method further includes subjecting the sample of arylsulfatase A to viral inactivation, e.g., by contacting the arylsulfatase A with a solvent or detergent. The solvent or detergent can include, for example, polysorbate 80, Tri-n-Butyl-Phosphate (TnBP), or both.

In some embodiments, the method further includes subjecting the sample of arylsulfatase to anion exchange chromatography, e.g., quaternary amine anion exchange chromatography, e.g., as described herein. In some embodiments, the sample of arylsulfatase A is subjected to the anion exchange chromatography prior to cation exchange chromatography.

In some embodiments, the method further includes subjecting the sample of arylsulfatase A to mixed mode chromatography, e.g., HA chromatography, e.g., as described herein. For example, the mixed mode chromatography can include ceramic hydroxyapatite chromatography. In some embodiments, the sample is subjected to the mixed mode chromatography, prior to the cation exchange chromatography.

In some embodiments, the method further includes subjecting the sample to hydrophobic interaction chromatography (HIC), such as HIC including phenyl chromatography, e.g., as described herein. In some embodiments, the sample is subjected to HIC prior to the cation exchange chromatography.

In some embodiments, the method further includes concentrating the arylsulfatase A, e.g., by ultrafiltration, diafiltration, or both. In some embodiments, concentrating the arylsulfatase A includes tangential flow ultrafiltration.

In some embodiments, the method further includes subjecting the sample arylsulfatase A to viral removal filtration, e.g., by using a PLANOVA™ filter.

In some embodiments, the method further includes formulating the purified arylsulfatase A. The buffer used for formulating the purified arylsulfatase A can include, for example, sodium chloride.

In one aspect, the disclosure features a method of purifying arylsulfatase A from a sample, where the method includes, for example, providing a sample of arylsulfatase A; subjecting the sample of arylsulfatase A to a first ion exchange chromatography; subjecting the sample of arylsulfatase A to mixed mode chromatography, e.g., as described herein; subjecting the sample of arylsulfatase A to hydrophobic interaction chromatography, e.g., as described herein; and subjecting the sample of arylsulfatase A to a second ion exchange chromatography. In one embodiment, the first ion exchange chromatography includes anion exchange chromatography, e.g., as described herein. In another embodiment, the second ion exchange chromatography includes cation exchange chromatography, e.g., as described herein, such as sulfopropyl (SP) cation exchange chromatography.

In one embodiment, the method further includes subjecting the sample of arylsulfatase A to depth filtration, e.g., a depth filtration described herein. In another embodiment, the method further includes subjecting the sample of arylsulfatase A to viral inactivation, e.g., a viral inactivation method described herein.

In another embodiment, the method further includes concentrating the arylsulfatase A, e.g., by a method described herein, and in another embodiment, the method further includes subjecting the arylsulfatase A product to viral removal filtration, e.g., by a method described herein.

In yet another embodiment, the method further includes formulating the purified arylsulfatase A.

In one aspect, the disclosure features a method of purifying arylsulfatase A from a sample, where the method includes, e.g., providing a sample of arylsulfatase A; subjecting the sample of arylsulfatase A to a first ion exchange chromatography (e.g., anion exchange chromatography, e.g., as described herein) to obtain an ion exchange chromatography sample of arylsulfatase A; subjecting the ion exchange chromatography sample of arylsulfatase A to mixed mode chromatography, e.g., as described herein, to obtain a mix mode chromatography sample of aryl sulfatase A; subjecting the mix mode chromatography sample of arylsulfatase A to hydrophobic interaction chromatography, e.g., as described herein, to obtain a hydrophobic interaction chromatography sample of arylsulfatase A; and subjecting the hydrophobic interaction chromatography sample of arylsulfatase A to a second ion exchange chromatography (e.g., cation exchange chromatography, e.g., as described herein).

In some embodiments, the first ion exchange chromatography comprises anion exchange chromatography, e.g., as described herein, and the second ion exchange chromatography includes cation exchange chromatography, e.g., as described herein, such as sulfopropyl (SP) cation exchange chromatography described herein.

In one embodiment, the method further includes subjecting the sample of arylsulfatase A to depth filtration, e.g., by a method described herein. In another embodiment, the method further comprises subjecting the sample to viral inactivation, e.g., by a method described herein.

In one embodiment, the method further includes concentrating the arylsulfatase A, e.g., by a method described herein. In another embodiment, the method includes subjecting the arylsulfatase A product to viral removal filtration, e.g., by a method described herein.

In yet another embodiment, the method further includes formulating the purified arylsulfatase A.

In one aspect, the disclosure features a method of formulating arylsulfatase A purified by a method herein. For example, the purified arylsulfatase A is formulated for direct delivery to the central nervous system (CNS), e.g., via intrathecal or intracerebral delivery, or for delivery by other means, e.g., intravenous (IV) delivery, or both, either concurrently, sequentially, or otherwise combinatory according to a treatment paradigm determined by a physician on a patient by patient basis, to treat a disease described herein, e.g., metachromatic leukodystrophy (MLD).

In another aspect, the disclosure features a pharmaceutical composition containing arylsulfatase A purified by a method herein, e.g., for direct delivery to the central nervous system (CNS), e.g., via intrathecal or intracerebral delivery, or for delivery by other means, e.g., intravenous (IV) delivery, or both, either concurrently, sequentially, or otherwise combinatory according to a treatment paradigm determined by a physician on a patient by patient basis, to treat a disease described herein, e.g., metachromatic leukodystrophy (MLD).

In yet another aspect, the disclosure features use of a composition containing arylsulfatase A purified by a method herein, e.g., for direct delivery to the central nervous system (CNS), e.g., via intrathecal or intracerebral delivery, or for delivery by other means, e.g., intravenous (IV) delivery, or both, either concurrently, sequentially, or otherwise combinatory according to a treatment paradigm determined by a physician on a patient by patient basis, to treat a disease described herein, e.g., metachromatic leukodystrophy (MLD).

In still another aspect, the invention features a method for administering a pharmaceutical composition containing arylsulfatase A purified by a method herein to a subject, e.g., to treat a disease described herein, e.g., metachromatic leukodystrophy (MLD).

DETAILED DESCRIPTION

Arylsulfatase A

Arylsulfatase A (ASA, ARSA, or cerebroside-sulfatase) is an enzyme that breaks down cerebroside 3-sulfate (or sulfatide) into cerebroside and sulfate. Specifically, galactosyl sulfatide is normally metabolized by the hydrolysis of 3-O-sulphate linkage to form galactocerebroside through the combined action of the lysosomal enzyme arylsulfatase A (EC 3.1.6.8) (Austin et al. *Biochem J.* 1964, 93, 15C-17C) and a sphingolipid activator protein called saposin B. A deficiency of arylsulfatase A occurs in all tissues from patients with the late infantile, juvenile, and adult forms of metachromatic leukodystrophy (MLD). As used herein, the arylsulfatase A protein will be termed "ASA" or "ARSA" and the saposin B will be termed "Sap-B".

Arylsulfatase A is an acidic glycoprotein with a low isoelectric point. Above pH 6.5, the enzyme exists as a monomer with a molecular weight of approximately 100 kDa. Arylsulfatase A undergoes a pH-dependent polymerization forming a dimer at pH 4.5. In human urine, the enzyme consists of two non-identical subunits of 63 and 54 kDa (Laidler P M et al. *Biochim Biophys Acta.* 1985, 827, 73-83). Arylsulfatase A purified from human liver, placenta, and fibroblasts also consist of two subunits of slightly different sizes varying between 55 and 64 kDa (Draper R K et al. *Arch Biochemica Biophys.* 1976, 177, 525-538, Waheed A et al. *Hoppe Seylers Z Physiol Chem.* 1982, 363, 425-430, Fujii T et al. *Biochim Biophys Acta.* 1992, 15 1122, 93-98). As in the case of other lysosomal enzymes, arylsulfatase A is synthesized on membrane-bound ribosomes as a glycosylated precursor. It then passes through the endoplasmic reticulum and Golgi, where its N-linked oligosaccharides are processed with the formation of phosphorylated and sulfated oligosaccharide of the complex type (Waheed A et al. *Biochim Biophys Acta.* 1985, 847, 53-61, Braulke T et al. *Biochem Biophys Res Commun.* 1987, 143, 178-185). In normal cultured fibroblasts, a precursor polypeptide of 62 kDa is produced, which translocates via mannose-6-phosphate receptor binding (Braulke T et al. *J Biol Chem.* 1990, 265, 6650-6655) to an acidic prelysosomal endosome (Kelly B M et al. *Eur J Cell Biol.* 1989, 48, 71-78).

The methods described herein can be used to purify arylsulfatase A from any source, e.g., from tissues, or cultured cells (e.g., human cells (e.g., fibroblasts) that recombinantly produce arylsulfatase A). Arylsulfatase A of any origin, including, but not limited to human and other animals, such as mammals, can be produced by the methods described herein.

The length (18 amino acids) of the human arylsulfatase A signal peptide is based on the consensus sequence and a specific processing site for a signal sequence. Hence, from the deduced human ASA cDNA (EMBL GenBank accession numbers J04593 and X521151) the cleavage of the signal peptide occurs in all cells after residue number 18 (Ala), resulting in the mature form of the human arylsulfatase A. As used herein, recombinant arylsulfatase A will be abbreviated "rASA". The mature form of arylsulfatase A including the mature form of human arylsulfatase A will be termed "mASA" and the mature recombinant human ASA will be termed "mrhASA".

Multiple forms of arylsulfatase A have been demonstrated on electrophoresis and isoelectric focusing of enzyme preparations from human urine (Luijten J A F M et al. *J Mol Med.* 1978, 3, 213), leukocytes (Dubois et al. *Biomedicine.* 1975, 23, 116-119, Manowitz P et al. *Biochem Med Metab Biol.* 1988, 39, 117-120), platelets (Poretz et al. *Biochem J.* 1992, 287, 979-983), cultured fibroblasts (Waheed A et al. *Hoppe Seylers Z Physiol Chem.* 1982, 363, 425-430, Stevens R L et al. *Biochim Biophys Acta.* 1976, 445, 661-671, Farrell D F et al. *Neurology.* 1979, 29, 16-20) and liver (Stevens R L et al. *Biochim Biophys Acta.* 1976, 445, 661-671, Farrell D F et al. *Neurology.* 1979, 29, 16-20, Sarafian T A et al. *Biochem Med.* 1985, 33, 372-380). Treatment with endoglycosidase H, sialidase, and alkaline phosphatase reduces the molecular size and complexity of the electrophoretic pattern, which suggests that much of the charge heterogeneity of arylsulfatase A is due to variations in the carbohydrate content of the enzyme.

The active site of arylsulfatase A contains an essential histidine residue (Lee G D and Van Etten R L, *Arch Biochem Biophys.* 1975, 171, 424-434) and two or more arginine residues (James G T, *Arch Biochem Biophys.* 1979, 97, 57-62). Many anions are inhibitors of the enzyme at concentrations in the millimolar range or lower.

A protein modification has been identified in two eukaryotic sulfatases (arylsulfatase A and arylsulfatase B (ASB)) and for one from the green alga *Volvox carteri* (Schmidt B et al. *Cell.* 1995, 82, 271-278, Selmer T et al. *Eur J Biochem.* 1996, 238, 341-345). This modification leads to the conversion of a cysteine residue, which is conserved among the known sulfatases, into a 2-amino-3-oxopropionic acid residue (Schmidt B et al. *Cell.* 1995, 82, 271-278). The novel amino acid derivative is also recognized as C-formylglycine (FGly). In arylsulfatase A and arylsulfatase B derived from MSD cells, the Cys-69 residue is retained. Consequently, it is proposed that the conversion of the Cys-69 to FGly-69 is required for generating catalytically active arylsulfatase A and arylsulfatase B, and that deficiency of this protein modification is the cause of MSD. Cys-69 is referred to the precursor arylsulfatase A which has an 18 residue signal peptide. In the matured arylsulfatase A (mASA) the mentioned cysteine residue is Cys-51.

Further investigations have shown that a linear sequence of 16 residues surrounding the Cys-51 in the matured arylsulfatase A is sufficient to direct the conversion and that the protein modification occurs after or at a late stage of co-translational protein translocation into the endoplasmic reticulum when the polypeptide is not yet folded to its native structure (Dierks T et al. *Proc Natl Acad Sci.* 1997, 94, 11963-1196, Wittke, D. et al. (2004), *Acta Neuropathol. (Berl.)*, 108, 261-271).

The human arylsulfatase A gene structure has been described. As used herein, this gene will be termed "ARSA." However, "ARSA" may also refer to arylsulfatase A protein in some cases. The ARSA gene is located near the end of the long arm of chromosome 22 (22q13.31-qter), it spans 3.2 kb (Kreysing et al. *Eur J Biochem.* 1990, 191, 627-631) and consists of eight exons specifying the 507 amino acid enzyme unit (Stein et al. *J Biol Chem.* 1989, 264, 1252-1259). Messenger RNAs of 2.1, 3.7, and 4.8 kb have been detected in fibroblast cells, with the 2.1-kb message apparently responsible for the bulk of the active arylsulfatase A generated by the cell (Kreysing et al. *Eur J Biochem.* 1990, 191, 627-631). The ARSA sequence has been deposited at the EMBL GenBank with the accession number X521150. Differences between the published cDNA and the coding part of the ARSA were described by Kreysing et al. (*Eur J Biochem.* 1990, 191, 627-631). The cDNA sequence originally described by Stein et al. (*J Biol Chem.* 1989, 264, 1252-1259) and the cDNA sequence described by Kreysing et al. (*Eur J Biochem.* 1990, 191, 627-631) have been deposited at the EMBL GenBank with the following accession numbers J04593 and X521151, respectively.

Several polymorphisms and more than 40 disease-related mutations have been identified in the ARSA gene (Gieselmann et al. *Hum Mutat.* 1994, 4, 233-242, Barth et al. *Hum Mutat.* 1995, 6, 170-176, Draghia et al. *Hum Mutat.* 1997, 9, 234-242). The disease-related mutations in the ARSA gene can be categorized in two broad groups that correlate fairly well with the clinical phenotype of MLD. One group (I) produces no active enzyme, no immunoreactive protein, and expresses no ASA activity when introduced into cultured animal cell lines. The other group (A) generates small amounts of cross-reactive material and low levels of functional enzyme in cultured cells. Individuals homozygous for a group (I) mutation, or having two different mutations from this group, express late infantile MLD. Most individuals with one group (I)-type and one group (A)-type mutation develop the juvenile-onset form, whereas those with two group (A)-type mutations generally manifest adult MLD. Some of the mutations have been found relatively frequently, whereas others have been detected only in single families. It is possible to trace specific mutations through members of many families, however general carrier screening is not yet feasible.

In addition to the disease-related mutations described above, several polymorphisms have been identified in the ARSA gene. Extremely low ASA activity has been found in some clinically normal parents of MLD patients and also in the general population. This so-called pseudodeficiency ASA has been associated with a common polymorphism of the ARSA gene (Gieselmann et al. *Dev Neurosci.* 1991, 13, 222-227).

Purification of Arylsulfatase A

As used herein, a "contaminant" is a material that is different from the desired polypeptide product, e.g., arylsulfatase A (ASA). The contaminant may be a variant of the desired polypeptide (e.g., a deamidated variant or an aminoaspartate variant of the desired polypeptide) or another molecule, for example, polypeptide, nucleic acid, and endotoxin.

As used herein, by "purifying" a polypeptide from a composition or sample comprising the polypeptide and one or more contaminants is meant increasing the degree of purity of the polypeptide in the composition or sample by removing (completely or partially) at least one contaminant from the composition or sample. A "purification step" may be part of an overall purification process resulting in a composition comprising at least about 20%, 30%, 40%, 50%, 60%, 70%, 80%, 90%, 95%, 99%, 99.5%, 99.6%, 99.7%, 99.8%, or 99.9% by weight of the polypeptide of interest, based on total weight of the composition.

A starting material for the purification process can be from any source, e.g., a tissue or a crude cell extract. Typically, the ASA is secreted by the cells and is subsequently purified from the cell culture supernatant.

The purification methods described herein can include, but not limited to, one or more of the following steps: depth filtration, viral inactivation, ion exchange chromatography (e.g., anion exchange chromatography, and/or cation exchange chromatography), mixed mode chromatography, hydrophobic interaction chromatography, ultrafiltration/diafiltration, and viral removal filtration.

In the chromatography steps the appropriate volume of resin used when packed into a chromatography column is reflected by the dimensions of the column, i.e., the diameter of the column and the height of the resin, and varies depending on e.g., the amount of protein in the applied solution and the binding capacity of the resin used. However, it is within the scope of the present disclosure to increase the scale of the production process as well as the purification process in order to obtain production and purification of ASA on an industrial scale. Accordingly parameters such as column size, diameter, and flow rate can be increased in order to comply with the speed and efficiency of such large-scale production. In some embodiments, the diameter of the column ranges from about 50-100 mm, the volume ranges from about 100-300 ml, and flow rate is between about 40-400 cm/hour (e.g., between about 100 cm/hour and 150 cm/hour) or about 5 to 100 ml.

Depth Filtration

The purification methods described herein can include one or more steps of depth filtration. Depth filters are the variety of filters that use a porous filtration medium to retain particles throughout the medium, rather that just on the surface of the medium. These filters are commonly used when the fluid to be filtered contains a high load of particles because, relative to other types of filters, they can retain a large mass of particles before becoming clogged. An exemplary depth filter is ZETA PLUS® depth filter.

Viral Inactivation

The purification methods described herein can include one or more steps of viral inactivation.

It is understood that these methods are intended to give rise to a preparation of an enzyme, which is substantially free of infectious viruses and which can be denoted a "virus-safe product". In addition, it is contemplated that the various methods can be used independently or in combination.

Virus-inactivation can be accomplished by the addition of one or more "virus-inactivating agents" to a solution comprising the enzyme. Typically, the virus-inactivating step will be performed prior to the chromatographic purification steps in order to assure that the agent is not present in the final product in any amounts or concentrations that will compromise the safety of the product when used as a pharmaceutical or when the product is used for the preparation of a pharmaceutical. The term "virus-inactivating agent" is intended to denote such an agent or a method, which can be used in order to inactivate lipid-enveloped viruses as well as non-lipid enveloped viruses. The term "virus-inactivating agent" is to be understood as encompassing both a combination of such agents and/or methods, whenever that is appropriate, as well as only one type of such agent or method.

Typical virus-inactivating agents are detergents and/or solvents, most typically detergent-solvent mixtures. It is to be understood that the virus inactivating agent is optionally a mixture of one or more detergents with one or more solvents. A wide variety of detergents and solvents can be used for virus inactivation. The detergent may be selected from the group consisting of non-ionic and ionic detergents and is selected to be substantially non-denaturing. Typically, a non-ionic detergent is used as it facilitates the subsequent elimination of the detergent from the rASA preparation in the subsequent purification steps. Suitable detergents are described, e.g. by Shanbrom et al., in U.S. Pat. Nos. 4,314,997, and 4,315,919. Typical detergents are those sold under the trademarks Triton X-100 and Tween 20 or Tween 80. Preferred solvents for use in virus-inactivating agents are di- or tri-alkylphosphates as described e.g. by Neurath and Horowitz in U.S. Pat. No. 4,764,369. A typical solvent is tri(n-butyl)phosphate (TnBP). An especially preferred virus-inactivating agent for the practice of the present invention is Tween 80, but, alternatively, other agents or combinations of agents can be used. The typical agent added in such a volume that the concentration of Tween-80 in the ASA-containing solution is within the range of about 0.5-4.0% by weight, preferably at a concentration of about 1% by weight. TnBP can then be added to a final concentration of 0.3% calculated based on the new volume of the sample containing ASA.

The virus-inactivation step is conducted under conditions inactivating enveloped viruses resulting in a substantially virus-safe rASA-containing solution. In general, such conditions include a temperature of 4-37° C., such as 19-28° C., 23-27° C., typically about 25° C., and an incubation time found to be effective by validation studies. Generally, an incubation time of 1-24 hours is sufficient, preferably 10-18 hours, such as about 14 hours, to ensure sufficient virus inactivation. However, the appropriate conditions (temperature and incubation times) depend on the virus-inactivating agent employed, pH, and the protein concentration and lipid content of the solution.

It is contemplated that other methods for removal of or inactivating virus can also be employed to produce a virus-safe product, such as the addition of methylene blue with subsequent inactivation by radiation with ultraviolet light.

Ion Exchange Chromatography

The purification methods described herein can include one or more steps of ion exchange chromatography (e.g., anion exchange chromatography and/or cation exchange chromatography).

As will be known by the person skilled in the art, ion exchangers (e.g., anion exchangers and/or cation exchangers) may be based on various materials with respect to the matrix as well as to the attached charged groups. For example, the following matrices may be used, in which the materials mentioned may be more or less crosslinked: agarose based (such as SEPHAROSE™ CL-6B, SEPHAROSE™ Fast Flow and SEPHAROSE™ High Performance), cellulose based (such as DEAE SEPHACEL®), dextran based (such as SEPHADEX®), silica based and synthetic polymer based.

The ion exchange resin can be prepared according to known methods. Typically, an equilibration buffer, which allows the resin to bind its counter ions, can be passed through the ion exchange resin prior to loading the sample or composition comprising the polypeptide and one or more contaminants onto the resin. Conveniently, the equilibration buffer can be the same as the loading buffer, but this is not required.

In an optional embodiment of the invention, the ion exchange resin can be regenerated with a regeneration buffer after elution of the polypeptide, such that the column can be re-used. Generally, the salt concentration and/or pH of the regeneration buffer can be such that substantially all contaminants and the polypeptide of interest are eluted from the ion exchange resin. Generally, the regeneration buffer has a very high salt concentration for eluting contaminants and polypeptide from the ion exchange resin.

Anion Exchange Chromatography

For the anion exchange resin, the charged groups which are covalently attached to the matrix can be, for example, diethylaminoethyl (DEAE), quaternary aminoethyl (QAE), and/or quaternary ammonium (Q). In some embodiments, the anion exchange resin employed is a Q Sepharose column, and more typically, it can be a Q SEPHAROSE™ Fast Flow, Q SEPHAROSE™ High Performance, or Q SEPHAROSE™ XL column, but other anion exchangers can be used.

The aqueous solution comprising the ASA and contaminant(s) can be loaded onto the anionic resin using a loading buffer that has a salt concentration and/or a pH such that the polypeptide and the contaminant bind to the anion exchange resin. The resin can then be washed with one or more column volumes of loading buffer followed by one or more column volumes of wash buffer wherein the salt concentration is increased. Finally, the ASA can be eluted by further increasing the salt concentration. Optionally, elution of the enzyme may also be mediated by gradually or stepwise decreasing the pH. The fractions containing ASA activity can be collected and combined for further purification.

It is apparent to the person of ordinary skill in the art that numerous different buffers may be used in the loading, washing, and elution steps. Typically, however, the column can be equilibrated with 1-10 column washes of a buffer comprising 0.05 M MES-Tris, pH 7.0. As of convenience the sample can be loaded in the buffer from the previous step of the purification process, or the sample can be loaded using a loading buffer. The column can be washed with 1-10 column volumes of the buffer used for equilibration, followed by a washing buffer comprising 0.02 MES-Tris, 0.12 M NaCl, pH 7.0. Alternatively, the column can be equilibrated, loaded, and washed with any other equilibration, loading, and washing buffers described herein for anion exchange chromatography. The sample can be eluted in a buffer comprising 0.02 MES-Tris, 0.26 M NaCl, pH 7.0. Alternatively, the sample can be eluted in any other elution buffer described herein for anion exchange chromatography.

Cation Exchange Chromatography

In a typical embodiment, the cation exchange chromatography comprises sulfopropyl (SP) cation exchange chromatography, but other cation chromatography membranes or resins can be used, for example, a MUSTANG™ S membrane, an S-SEPHAROSE™ resin, or a Blue SEPHAROSE™ resin.

In some embodiments, the cation exchange chromatography is used as a polishing step.

The aqueous solution comprising the arylsulfatase A and contaminant(s) can be loaded onto the cationic resin using a loading buffer that has a salt concentration and/or a pH such that the polypeptide and the contaminant bind to the cation exchange resin. The resin can then be washed with one or more column volumes of equilibration butter or loading buffer, and optionally followed by one or more column volumes of wash buffer wherein the salt concentration is increased. Finally, the arylsulfatase A can be eluted in an elution buffer. The fractions containing arylsulfatase A activity can be collected and combined for further purification.

In a typical embodiment, the NaCl concentration and/or pH of the loading buffer, washing buffer, and/or elution buffer, can be optimized, e.g., as described herein, to enhance target binding and/or decrease impurity binding. In some embodiments, the NaCl concentration in the loading buffer is about 20 mM, 15 mM, 10 mM, or less. In some embodiments, the loading buffer has a pH of about 4.5, 4.3, 4.0, or less. In some embodiments, the NaCl concentration in the washing buffer is about 20 mM, 15 mM, 10 mM, or less. In some embodiments, the NaCl concentration in the elution buffer is about 55 mM, 50 mM, 45 mM, 40 mM, or less.

In some embodiments, the columns can be equilibrated with more than 3, e.g., 5 to 10 column volumes of 0.01 M NaAc, 0.01 M NaCl, 0.03 M acetic acid, pH 4.2. In some embodiment, the sample can be loaded in the buffer from the previous step of the purification process, or the sample can be loaded using a loading buffer. The column can be washed with 1-10 column volumes of the buffer used for equilibration. Alternatively, the column can be equilibrated, loaded, and washed with any other equilibration, loading, and washing buffers described herein for cation exchange chromatography. The sample can be eluted in a buffer comprising 0.02 M NaAc, 0.05 M NaCl, pH 4.5. Alternatively, the sample can be eluted in any other elution buffer described herein for cation exchange chromatography.

In another typical embodiment, the cation exchange chromatography can be performed at an optimized temperature, e.g., as described herein, to enhance target binding and/or decrease impurity binding. For example, the cation exchange chromatography can be performed at a temperature of about 23° C., 18° C., 16° C., or less.

Mixed-Mode Chromatography

The purification methods described herein can include one or more steps of mixed-mode chromatography.

Mixed-mode chromatography is a type of chromatography in which several modes of separation are applied to resolve a mixture of different molecules, typically in liquid chromatography. For example, a mixed-mode separation can include combinational phases with ion-exchange and reversed phase characteristics at the same time. These stationary phases with more than one interaction type are available from several column manufacturers.

In some embodiments, the mixed-mode chromatography includes ceramic hydroxyapatite (HA) chromatography. Hydroxyapatite (HAP) usually refers to the crystalline form of calcium phosphate. The mechanism of HAP involves non-specific interactions between negatively charged protein carboxyl groups and positively charged calcium ions on the resin, and positively charged protein amino groups and negatively charged phosphate ions on the resin. Basic or acidic proteins can be adsorbed selectively onto the column by adjusting the buffer's pH; elution can be achieved by varying the buffer's salt concentration. Again, it is evident that numerous buffer compositions as well as combinations of buffers can be employed. Typically, however, the column can be equilibrated with 1-10 column washes of a buffer comprising 0.001 M $NaPO_4$, 0.02 M MES-Tris, 0.26 M NaCl, pH 7.0. As of convenience the sample can be loaded in the buffer from the previous step of the purification process, or the sample can be loaded using a loading buffer. The column can be washed with 1-10 column volumes of the buffer used for equilibration, followed by a washing buffer comprising 0.005 M $NaPO_4$, 0.02 M MES-Tris, 0.26 M NaCl, pH 7.0. Alternatively, the column can be equilibrated, loaded, and washed with any other equilibration, loading, and washing buffers described herein for mixed mode chromatography. The sample can be eluted in a buffer comprising 0.04 M $NaPO_4$, pH 7.0. Optionally, the column can be stripped by washing with 1-10 column volumes of 0.4 M $NaPO_4$, pH 12. Alternatively, the sample can be eluted in any other elution buffer described herein for mixed mode chromatography.

In some embodiments, the purification of ASA by mixed mode chromatography succeeds the purification by ion-exchange chromatography (e.g., anion exchange chromatography). It is contemplated, however, that these steps could be performed in the reverse order.

Hydrophobic Interaction Chromatography (HIC)

The purification methods described herein can include one or more steps of hydrophobic interaction chromatography.

Hydrophobic interaction chromatography utilizes the attraction of a given molecule for a polar or non-polar environment, and in terms of protein, this propensity is governed by the hydrophobicity or hydrophilicity of residues on the exposed, outer surface of a protein. Thus, proteins are fractionated based upon their varying degrees of attraction to a hydrophobic matrix, typically an inert support with alkyl linker arms of 2-18 carbons in chain length. The stationary phase consists of small non-polar groups (butyl, octyl, or phenyl) attached to a hydrophilic polymer backbone (e.g., cross-linked SEPHAROSE™, dextran, or agarose). Thus, the HIC column is typically a butyl SEPHAROSE™ column or a phenyl SEPHAROSE™ column, most typically a phenyl SEPHAROSE™ column.

Loading, washing and elution in HIC basically follow the same principle as described above for the ion-exchange chromatography, but often nearly opposite conditions to those used in ion exchange chromatography are applied. Thus, the HIC process involves the use of a high salt loading buffer, which unravels the protein to expose hydrophobic sites. The protein is retained by the hydrophobic ligands on the column, and is exposed to a gradient of buffers containing decreasing salt concentrations. As the salt concentration decreases, the protein returns to its native conformation and eventually elutes from the column. Alternatively proteins may be eluted with PEG.

The use of phenyl SEPHAROSE™ as solid phase in the HIC is typical in the present disclosure. Again, it is readily apparent that, when it comes to the exact conditions as well as the buffers and combinations of buffers used for the loading, washing and elution processes, a large number of different possibilities exist. In a typical embodiment, the column can be equilibrated in a buffer which contains 0.05 M $NaPO_4$, 1 M NaCl, pH 5.5. As of convenience the sample can be loaded in the buffer from the previous step of the purification process, or the sample can be loaded using a loading buffer. Washing can be performed using 1-2 column washes of equilibration buffer followed by 1-5 column volumes of 0.02 M MES, 0.05 M $NaPO_4$, 0.5 M NaCl, pH 5.5. Alternatively, the column can be equilibrated, loaded, and washed with any other equilibration, loading, and washing buffers described herein for HIC. Arylsulfatase A can be eluted using 0.02 M MES-Tris, 0.06 M NaCl, pH 7.0. Alternatively, the sample can be eluted in any other elution buffer described herein for HIC.

In some embodiments, the purification of arylsulfatase A by HIC succeeds the purification by ion-exchange chromatography (e.g., anion exchange chromatography) and/or mixed mode chromatography. It is contemplated, however, that these steps could be performed in the reverse order.

Ultrafiltration/Diafiltration

The purification methods described herein can include one or more steps of ultrafiltration and/or diafiltration.

Ultrafiltration refers to a membrane separation process, driven by a pressure gradient, in which the membrane fractionates components of a liquid as a function of their solvated size and structure. Diafiltration is a specialized type of ultrafiltration process in which the retentate is diluted with water and re-ultrafiltered, to reduce the concentration of soluble permeate components and increase further the concentration of retained components.

In some embodiments, arylsulfatase A is purified by separation from contaminants according to their size in an acidic environment by tangential flow filtration. Arylsulfatase A forms an octamer at low pH with a theoretical molecular weight of 480 kDa and will therefore be retained by a relatively open membrane while most of the contaminants will pass this membrane (Sommerlade et al., (1994) *Biochem. J.*, 297; 123-130; Schmidt et al., (1995) *Cell*, 82 271-278; Lukatela et al., (1998) *Biochemistry*, 37, 3654-3664).

In a typical embodiment, the diafiltration buffer comprises 0.01 M sodium phosphate-citrate, 0.137 M NaCl, pH 6.0.

In some embodiment, as the starting material for this process is a suspension of arylsulfatase A as eluted from the chromatography column in the previous step of the process the pH in this suspension is adjusted to 4-5 by addition of 0.2-1 M Na-acetate pH 4.5. Diafiltration is then performed against 1-10 buffer volumes of Na-acetate pH 4.0-5.5 in a manner well known to somebody skilled in the art. The filtration can be performed with the application of several different filter types with nominal weight cut-off values ranging from 20-450 kDa, however it is typical to use a filter with a cut-off value ranging from 100-300 kDa. For further processing of the arylsulfatase A containing solution the pH is adjusted to a value within the range between 7 and 8 by addition of Tris-base to a final concentration of approximately 20-50 mM.

As an alternative to the acidic tangential flow filtration as described above, separation of ASA from the contaminants can be obtained with acidic gel filtration using essentially the same conditions and compositions of buffers. The filtration is performed at low pH through a gel filtration column, which has been equilibrated with a solution at low pH, for example, a 0.2-0.9 M solution of Na-acetate at pH 4-5. As an option, the solution of arylsulfatase A can be concentrated by tangential flow filtration through a 20-50 kDa filter prior to the gel filtration. The extent of concentration may vary considerably so that arylsulfatase A may be concentrated from about 0.1 mg/ml to about 50 mg/ml, preferably to about 5 mg/ml.

In some embodiments, the sample pool is concentrated against a Biomax A-screen, 30 kDa. Diafiltration is performed against 3-5 column washes of 20 mM Na-acetate, pH 5.4-5.7.

Viral Removal Filtration

The purification methods described herein can include one or more steps of viral removal filtration.

Typically, virus filtration is performed after purification of the enzyme by one or more steps of chromatography. In some embodiments, the virus filtration step is performed by passage of the ASA containing solution which is a result of a purification step through a sterile filter and subsequently passage of the sterile filtered solution through a nanofilter. By "sterile filter" is meant a filter, which will substantially remove all micro-organisms capable of propagating and/or causing infection. Whereas it is typical that the filter has a pore size of about 0.1 micron, the pore size could range between about 0.05 and 0.3 micron. It may be feasible to replace or combine virus filtration of the sample as performed in the purification process with contacting the sample with a detergent.

Formulation

The methods described herein can result in a product or formulation comprising a relative amount of bioactive arylsulfatase A, in particular arylsulfatase A which is at least 90%, such as at least 95%, at least 97%, at least 98%, at least 99%, at least 99.5%, at least 99.6%, at least 99.7%, at least 99.8%, or at least 99.9% of the total amount of proteins in the product or formulation as determined by reverse phase HPLC or size exclusion HPLC.

A therapeutic formulation comprising the polypeptide, optionally conjugated with a heterologous molecule, may be prepared by mixing the polypeptide having the desired degree of purity with optional pharmaceutically acceptable carriers, excipients or stabilizers (Remington's Pharmaceutical Sciences, 16th edition, Osol, A. Ed. (1980)), in the form of lyophilized formulations or aqueous solutions. "Pharmaceutically acceptable" carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride: phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polysorbate, poloxamers, or polyethylene glycol (PEG).

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. Ed. (1980).

Sustained-release preparations may be prepared. Suitable examples of sustained-release preparations include semipermeable matrices of solid hydrophobic polymers containing the polypeptide variant, which matrices are in the form of shaped articles, e.g., films, or microcapsule. Examples of sustained-release matrices include polyesters, hydrogels (for example, poly (2-hydroxyethyl-methacrylate), or poly (vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)3-hydroxybutyric acid.

The polypeptide purified as disclosed herein or the composition comprising the polypeptide and a pharmaceutically acceptable carrier is then used for various diagnostic, therapeutic or other uses known for such polypeptides and compositions. For example, the polypeptide may be used to treat a disorder in a mammal by administering a therapeutically effective amount of the polypeptide to the mammal.

In some embodiments, arylsulfatase A is formulated in an isotonic solution such as 154 mM NaCl, or 0.9% NaCl and 10-50 mM sodium phosphate pH 6.5-8.0 or sodium phosphate, glycine, mannitol or the corresponding potassium salts. In another embodiment, the ASA is formulated in a physiological buffer, such as:

a) formulation buffer I containing (in mM): $Na_2HPO_4$ (3.50-3.90), $NaH_2PO_4$ (0-0.5), Glycine (25-30), Mannitol (230-270), and water for injection; or b) formulation buffer II containing (in mM): Tris-HCl (10), Glycine (25-30), Mannitol (230-270), and water for injection.

The purified arylsulfatase A can be formulated for direct delivery to the central nervous system (CNS), e.g., via intrathecal or intracerebral delivery, or for delivery by other means, e.g., intravenous (IV) delivery, or both, either concurrently, sequentially, or otherwise combinatory according to a treatment paradigm determined by a physician on a patient by patient basis. For example, the pharmaceutical composition described herein can be administered by a route including intracerebroventricular, spinal, intrathecal, or intracranial administration. The pharmaceutical composition described herein can also be administered by a route other than intracerebroventricular, spinal, intrathecal or intracranial administration, such as a route selected from the group consisting of intravenous, intraarterial, oral, subcutaneous, intraperitoneal, intramuscular, intraparenchymal, mucosal, nasal, and rectal administration.

Arylsulfatase A purified by a method herein can be used as a medicament for reducing the sphingolipid 3-O-sulfogalgactosylceramide (galactosyl sulphatide) levels within cells in the peripheral nervous system and/or within the central nervous system in a subject suffering from and/or being diagnosed with metachromatic leukodystrophy. The administration of ASA will lead to decreased impairment of motor-learning skills and or to increased nerve motor conduction velocity and/or nerve conduction amplitude.

Intrathecal injection (that is injection directly into the cerebrospinal fluid) of recombinant human alpha-L-iduronidase (rhIDU) can reduce carbohydrate storage in brain tissue in a canine model of mucopolysaccharidosis (MPL) (Kakkis, 2003).

In some embodiments, the pharmaceutical composition described herein is administered directly to the CNS to a subject and thereby obtaining a reduction in target cells within the central nervous system in the subject.

In some embodiments, the pharmaceutical composition described herein is administered intravenously and/or by spinal injection to a subject and thereby obtaining a reduction in the galactosyl sulphatide levels in target cells within the peripheral nervous system and in target cells within the central nervous system in the subject.

In some embodiments, the arylsulfatase A described herein is efficiently endocytosed in vivo into target cells within a tissue selected from the group comprising CNS (e.g., oligodendroglia), peripheral nervous system (e.g., Schwann cells), liver, kidney, spleen, and heart.

It is contemplated that the exact nature of the treatment plans based on the method according to the present invention will depend on factors such as age, sex and disease stage of the subject to be treated, and that the optimal dosage regimen and frequency of administration may, with advantage, be determined on an empirical basis. For example, the pharmaceutical composition can be administered in one or more doses, each dose comprising an amount of arylsulfatase A which is within the range of about 0.1 to about 100 mg/kg body weight, such as within the range of about 0.25 to about 50, about 1 to about 25, about 1 to about 10, or about 1 to about 5 mg/kg body weight. The pharmaceutical composition can also be administered on a daily, weekly, bi-weekly or monthly basis.

The term "effective levels" is to be understood as levels of arylsulfatase A, which are effective in causing at least a 10% reduction of the stored sphingolipid 3-O-sulfogalgactosylceramide (galactosyl sulphatide) in cells within visceral organs, including the kidney, or within CNS, as determined e.g., by TLC 8 days after, e.g., intrathecal or intravenous administration of arylsulfatase A. It may be preferred that the reduction in galactosyl sulphatide is at least about 15%, at least about 20%, at least about 25%, at least about 30%, or at least about 40% relative to the levels present prior to administration of the enzyme. Also, it may be preferred that the arylsulfatase A is administered in an amount of between about 5 and 100 mg enzyme per kg of body weight, such as about 10 mg/kg body weight, about 20 mg/kg body weight, about 30 mg/kg body weight, about 50 mg/kg body weight, about 60 mg/kg body weight, about 70 mg/kg body weight, about 80 mg/kg body weight, or about 90 mg/kg body weight.

In some embodiments, the pharmaceutical composition described herein includes adjuncts and/or formulations with a known ability of facilitating delivery of macromolecules across the blood brain barrier.

In some embodiments, the use of adjuncts, such as compounds or formulations with a know ability to facilitate delivery of macromolecules to the central nervous system does not appear necessary in order to obtain the observed effect in the central nervous system. Thus, in some embodiments, the medicament does not comprise any of the following components:

a) a vehicle, such as a peptide or polypeptide, for delivery of the enzyme (arylsulfatase A) into the central nervous system, and b) a component capable of causing opening or disruption of the blood brain barrier, and c) an intact cell, including a transduced cell, such as a transduced autologous cell, such as transduced fibroblasts or peripheral blood lymphocytes.

In some embodiments, supplementary treatment with any of the above mentioned agents or components may be unnecessary. Therefore, in some embodiments, the medicament is for administration to a subject which does not receive any additional medical treatment for reduction of the sphingolipid 3-O— sulfogalgactosylceramide levels, including:

a) administration of a formulation comprising a vehicle, such as a peptide or polypeptide or antibody, for delivery of the enzyme (arylsulfatase A) into the central nervous system, and b) administration of a formulation capable of causing opening or disruption of the blood brain barrier, and c) administration of an intact cell, including a transduced cell, such as a transduced autologous cell, such as transduced fibroblasts or peripheral blood lymphocytes.

In a further embodiment, the pharmaceutical composition further comprises a hypertonic solution or is administered together with a hypertonic solution in order to cause osmotic opening of the blood-brain barrier.

Enzyme activity, which is to be understood as the catalytic activity of the ASA, may be measured in an enzyme assay based on the ASA mediated hydrolysis of either a detectable substrate or a substrate, which leads to a detectable end product. In one aspect, the assay is based on hydrolysis of the synthetic, chromogenic substrate, para-Nitrocatechol sulphate (pNCS) which has an end product, para-Nitrocatechol (pNC) that absorbs light at 515 nm.

For example, an arylsulfatase A enzyme assay can be:

Materials: 50 mM p-Nitrocatechol Sulphate: Dissolve 0.156 g p-Nitrocatechol Sulphate (Sigma, Catalogue # N-7251) in 10 ml double distilled (dd) H$_2$O, Store at 4° C. in foil.

3 M Sodium Acetate pH 5.0: Dissolve 24.69 g sodium acetate in 100 ml dd H2O, adjusted to pH 5 and store at room temperature.

4× Assay Buffer (should be made fresh on day of use): Mix 5.0 ml 3 M sodium acetate pH 5.0, 6.0 ml 50 mM p-Nitrocatechol Sulphate and 4.0 ml dd H$_2$O.

1 M NaOH: 4 g NaOH+100 ml dd H$_2$O, stored at room temperature.

Procedure: For screening purposes the assays were done in flat-bottomed Elisa plates. 25 of the 4× assay buffer was added to 75 µl of sample or an appropriate dilution of it. The plates were incubated overnight at 4° C., stopped with 200 µl of 1 M NaOH and the absorbance recorded at 515 nm on a plate reader.

For determination of specific activity of the DEAE-purified samples, the assays were set up in tubes with all the volumes doubled. Incubations were at 37° C. for periods ranging from 5-20 minutes using 10-1000 ng of enzyme. The samples were read on a spectrophotometer using a cuvette of 1 cm path length. Specific activity is defined as moles of p-Nitrocatechol Sulphate hydrolyse per minute per mg protein at 37° C., pH 5.0.

Calculations: One Unit (1 U) of enzyme activity is defined as the hydrolysis of 1 µmol p-Nitrocatechol Sulphate (pNCS) per minute at 37° C., pH 5.0.

The following equation is used in order to calculate the enzyme activity in µmol pNCS hydrolyzed/min×ml (=Units/ml):

$$\frac{V_{tot} \text{ (ml)}}{\varepsilon M / 1000 \times V_{sample} \text{ (ml)} \times \text{Incubation time (min)}} \times \Delta A = \text{Units/ml} \quad (1)$$

where:
ΔA=absorbance of sample−absorbance of blank
Vtot (ml)=total reaction volume in ml (in this case 0.15 ml)
Vsample (ml)=added sample volume in ml (in this case 0.05 ml)
εM=the molar extinction coefficient for the product pNC, which in this case is 12 400 M−1 cm−1

Equation 1 could more simplified be written as:

$$\Delta A \times (0.15/(12\,400/1000 \times 0.05 \times 30)) = X\,\mu\text{mol}/(\text{minute} \times \text{ml})(=\text{Units/ml}) \quad (1)$$

To calculate the specific activity in µmol pNC consumed/(minute×mg)(=Units/mg) divide equation 1 with the protein concentration of the sample:

$$\text{Eq. 1/Protein conc. (mg/ml)} = Y\,\mu\text{mol}/(\text{minute} \times \text{mg}) = \text{Units/mg} \quad (2)$$

Total protein concentration in in-process samples and final products may be determined by a commercially available assay that utilizes principles of the reduction of Cu$^{2+}$ to Cu$^+$ by proteins in an alkaline medium (the Biuret reaction). This method is well known to a person skilled in the art.

Concentration of arylsulfatase A in samples collected after various steps of the purification process may be assessed in arylsulfatase A enzyme linked immunosorbent assay (ELISA). Quantitative determination of a protein by ELISA is a conventional technique known to the person of ordinary skill in the art. However, it is within the scope of the present invention to provide a specific ELISA for the detection of rASA based on capturing the enzyme with specific polyclonal immunoglobulins and subsequently detecting the captured enzyme with specific monoclonal antibodies.

Purity and identity of the various preparations of arylsulfatase A may be determined by methods well known to the person of ordinary skill in the art, such as reverse phase HPLC, SDS-PAGE, and Western blot arylsulfatase A. In addition, the amount of whole cell proteins (HCP) in preparations of arylsulfatase A may be determined by the use of ELISA as well as Western blotting techniques using commercially available antibodies. Typically, all the above mentioned processes are adapted to be performed in microtiter plates for conveniency.

The arylsulfatase A product and the formulation comprising arylsulfatase A according to the present disclosure have as one of their characteristics a very low content of host cell proteins. In a product or formulation intended as a pharmaceutical composition or a product intended to be used in the preparation of a pharmaceutical composition the content of such proteins is critical since they are expected to have immunogenic effects. In a typical embodiment of the invention the final product or formulation contain less than 1.5% whole cell proteins, such as less than 1%, e.g., less than 0.75%, or less than 0.5%, or less than 0.25% whole cell proteins. The product or formulation may further contain impurities in the form of enzymatically inactive variants of the main component. In a typical embodiment the product or formulation according to the invention contains at least 90% enzymatically active ASA, such as 92% or 94%. In an even more typical embodiment, the relative amount of enzymatically active arylsulfatase A is at least 95%, such as 96% or 97% or even 98% or 99% as determined by reverse phase HPLC, or size exclusion HPLC.

A further characteristic of the enzyme or formulation prepared according to the process of the invention is its high level of specific activity. It is thus preferred that the formulation or pharmaceutical composition according to the disclosure comprises arylsulfatase A with a specific activity of at least 10 U/mg, at least 20 U/mg, at least 25 U/mg, at least 30 U/mg, at least 40 Umg, at least 50 U/mg, at least 60 U/mg, at least 70 U/mg, at least 75 U/mg, at least 80 U/mg, at least 85 U/mg, at least 90 U/mg, at least 100 U/mg, at least 150 U/mg, at least 200 U/mg, at least 250 U/mg, or at least 300 U/mg protein, e.g., as determined by a method described herein. Typically, the ASA has a specific activity of between about 50 U/mg to about 140 U/mg.

What is claimed:

1. A method of purifying recombinant arylsulfatase A (ASA) protein, comprising
    providing a sample of recombinant ASA protein;
    subjecting the sample to a first chromatography step which is anion exchange chromatography,
    subjecting the sample from the anion exchange chromatography to a second chromatography step which is mixed-mode chromatography,
    subjecting the sample from the mixed-mode chromatography to a third chromatography step which is hydrophobic interaction chromatography, and
    subjecting the sample from the hydrophobic interaction chromatography to a fourth chromatography step which is cation exchange chromatography,
    wherein fractions from each chromatography step containing recombinant ASA protein are determined by detecting the presence of recombinant ASA protein or enzymatic activity, and
    wherein the purified recombinant ASA protein has a specific activity of at least 75 U/mg,
    wherein 1 Unit of enzyme activity is defined as the hydrolysis of 1 μmol p-Nitrocatechol Sulphate (pNCS) per minute at 37° C., pH 5.0.

2. The method of claim 1, wherein the sample of recombinant ASA protein is obtained from cultured cell extract or cell culture supernatant.

3. The method of claim 1, wherein the cation exchange chromatography is sulfopropyl (SP) cation exchange chromatography.

4. The method of claim 1, wherein the mixed-mode chromatography is hydroxyapatite (HA) chromatography.

5. The method of claim 1, wherein the hydrophobic interaction chromatography is phenyl chromatography.

* * * * *